US010598603B2

(12) United States Patent
Masumura

(10) Patent No.: US 10,598,603 B2
(45) Date of Patent: Mar. 24, 2020

(54) LIGHTING DEVICE FOR INSPECTION AND INSPECTION SYSTEM

(71) Applicant: MACHINE VISION LIGHTING INC., Tokyo (JP)

(72) Inventor: Shigeki Masumura, Tokyo (JP)

(73) Assignee: MACHINE VISION LIGHTING INC., Tokyo (JP)

( * ) Notice: Subject to any disclaimer, the term of this patent is extended or adjusted under 35 U.S.C. 154(b) by 0 days.

(21) Appl. No.: 15/580,087

(22) PCT Filed: Sep. 23, 2015

(86) PCT No.: PCT/JP2015/076824
§ 371 (c)(1),
(2) Date: Dec. 6, 2017

(87) PCT Pub. No.: WO2017/051447
PCT Pub. Date: Mar. 30, 2017

(65) Prior Publication Data
US 2018/0299386 A1 Oct. 18, 2018

(30) Foreign Application Priority Data

Sep. 22, 2015 (JP) ................................. 2015-186170

(51) Int. Cl.
*G01N 21/88* (2006.01)
*G01N 21/956* (2006.01)

(52) U.S. Cl.
CPC ... *G01N 21/8806* (2013.01); *G01N 21/95623* (2013.01); *G01N 2201/0636* (2013.01)

(58) Field of Classification Search
CPC ................................................ G01N 21/8806
(Continued)

(56) References Cited

U.S. PATENT DOCUMENTS 4,037,965 A * 7/1977 Weiss ................. G01N 15/0211
356/336
4,275,960 A * 6/1981 Habegger .............. H04N 1/029
355/68
(Continued)

FOREIGN PATENT DOCUMENTS

DE 112013005764 T5 10/2015
EP 0735361 A2 10/1996
(Continued)

OTHER PUBLICATIONS

European Search Report dated Jul. 3, 2018.

*Primary Examiner* — Tarifur R Chowdhury
*Assistant Examiner* — Omar H Nixon
(74) *Attorney, Agent, or Firm* — Dilworth & Barrese, LLP.; Michael J. Musella, Esq.

(57) ABSTRACT

Provided is an inspection lighting device with which, even when changes in light that occur at respective feature points on an object to be inspected are small, the amounts of those changes in light can be determined across the entire field-of-view range, and the feature points can be detected under exactly the same conditions. An inspection lighting device 100 includes a surface light source 1 and a lens 2 that is disposed between the surface light source 1 and an inspection object W, the lens 2 being disposed nearer to the inspection object W such that at least one of a shielding mask M1 and a filtering means F1 is located centered around a focal distance position of the lens. An irradiation solid angle of light emitted from the surface light source 1 and irradiated onto the inspection object W by the lens 2 is configured to have solid angle regions as desired, the solid angle regions having specific optical attributes. The shapes, sizes, and inclination angles of irradiation solid angles of the inspection light as well as solid angle regions having specific optical attributes within the irradiation solid angles can be set to be substantially uniform across the entire field of view in accordance with changes that occur at feature points on the inspection object.

18 Claims, 11 Drawing Sheets

*1 Outer housing of inspection lighting device is schematically indicated by dotted lines.

*2 First shielding mask M1 denotes mask of shielding portion, F1 denotes portion, within aperture, that transmits only light having specific wavelength band or polarization or that has specific transmittance, and F3 denotes irradiation solid angle forming means as a whole that integrates both. (see FIG. 4)

(58) Field of Classification Search
USPC .................................................... 356/237.1
See application file for complete search history.

(56) References Cited

U.S. PATENT DOCUMENTS

| | | | |
|---|---|---|---|
| 6,286,969 B1 | 9/2001 | Kurokawa et al. | |
| 6,980,377 B1* | 12/2005 | Larson | G02B 13/16 |
| | | | 359/722 |
| 7,295,303 B1* | 11/2007 | Vaez-Iravani | G01N 21/95623 |
| | | | 356/237.1 |
| 8,891,087 B2* | 11/2014 | Zuzak | G01N 21/31 |
| | | | 356/445 |
| 9,494,422 B2 | 11/2016 | Masumura | |
| 2001/0000679 A1* | 5/2001 | Vaez-Iravani | G01J 3/44 |
| | | | 356/237.1 |
| 2004/0262529 A1* | 12/2004 | Yoshida | G01N 21/8806 |
| | | | 250/372 |
| 2005/0036143 A1* | 2/2005 | Huang | G01B 11/0641 |
| | | | 356/369 |
| 2005/0110986 A1* | 5/2005 | Nikoonahad | G01N 21/94 |
| | | | 356/237.2 |
| 2006/0007436 A1* | 1/2006 | Kurosawa | G01N 21/47 |
| | | | 356/237.4 |
| 2006/0238754 A1* | 10/2006 | Fukazawa | G01N 21/956 |
| | | | 356/237.2 |
| 2007/0030477 A1* | 2/2007 | Hwang | G01N 21/45 |
| | | | 356/237.1 |
| 2008/0043313 A1* | 2/2008 | Ambar | G02B 27/46 |
| | | | 359/234 |
| 2012/0050739 A1* | 3/2012 | Hayano | G01B 11/24 |
| | | | 356/369 |
| 2014/0016125 A1* | 1/2014 | Sullivan | G01N 21/9501 |
| | | | 356/237.5 |
| 2014/0055780 A1* | 2/2014 | Ogawa | G01N 21/956 |
| | | | 356/237.5 |
| 2014/0078379 A1* | 3/2014 | Masuda | H04N 9/045 |
| | | | 348/360 |
| 2014/0210983 A1* | 7/2014 | Shimura | G02B 21/0016 |
| | | | 348/80 |
| 2015/0316488 A1 | 11/2015 | Masumura | |
| 2016/0139059 A1* | 5/2016 | Matsumoto | G01N 21/956 |
| | | | 356/51 |

FOREIGN PATENT DOCUMENTS

| | | |
|---|---|---|
| JP | 2013-120099 A | 6/2013 |
| WO | 2013/084755 A1 | 6/2013 |
| WO | 2014087868 A1 | 6/2014 |

* cited by examiner

FIG. 1

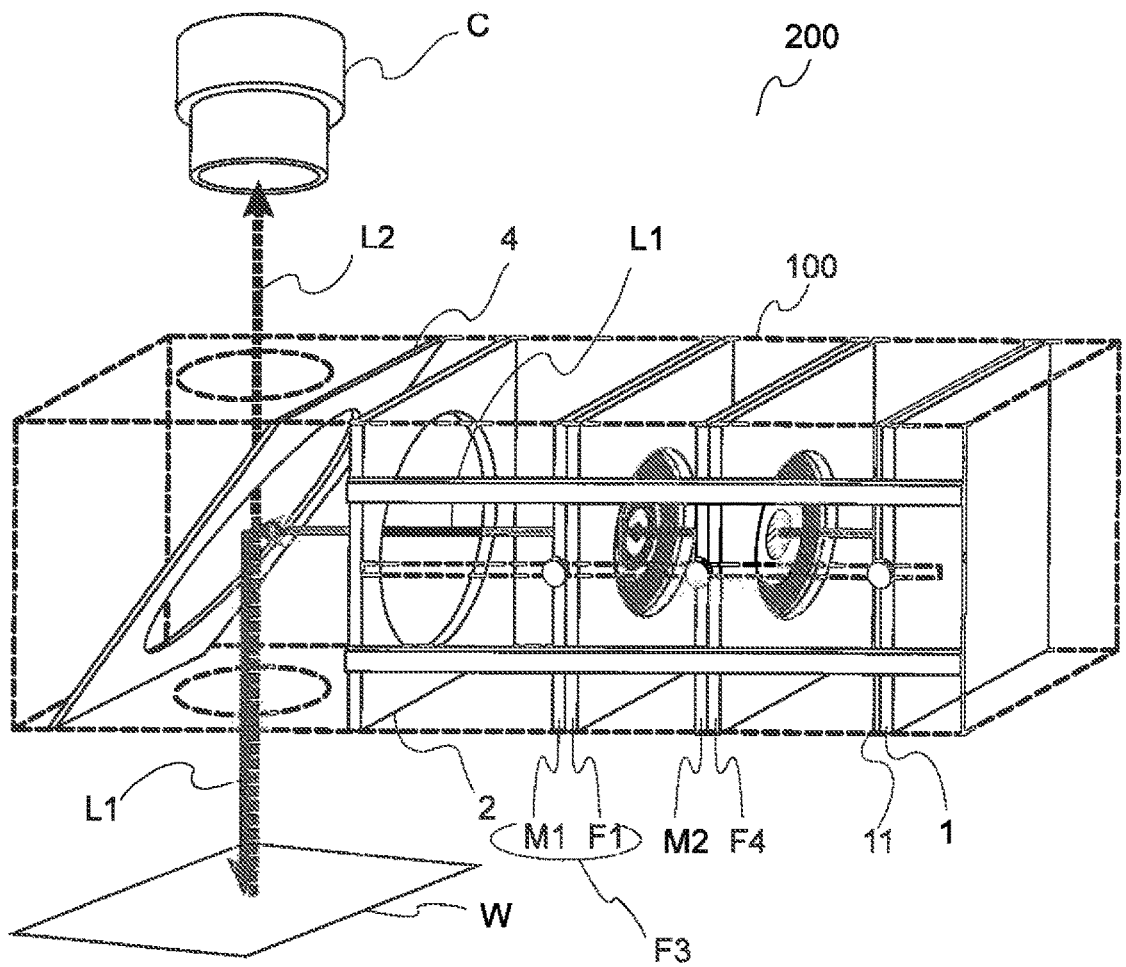

*1 Outer housing of inspection lighting device is schematically indicated by dotted lines.

*2 First shielding mask M1 denotes mask of shielding portion, F1 denotes portion, within aperture, that transmits only light having specific wavelength band or polarization or that has specific transmittance, and F3 denotes irradiation solid angle forming means as a whole that integrates both. (see FIG. 4)

FIG. 2

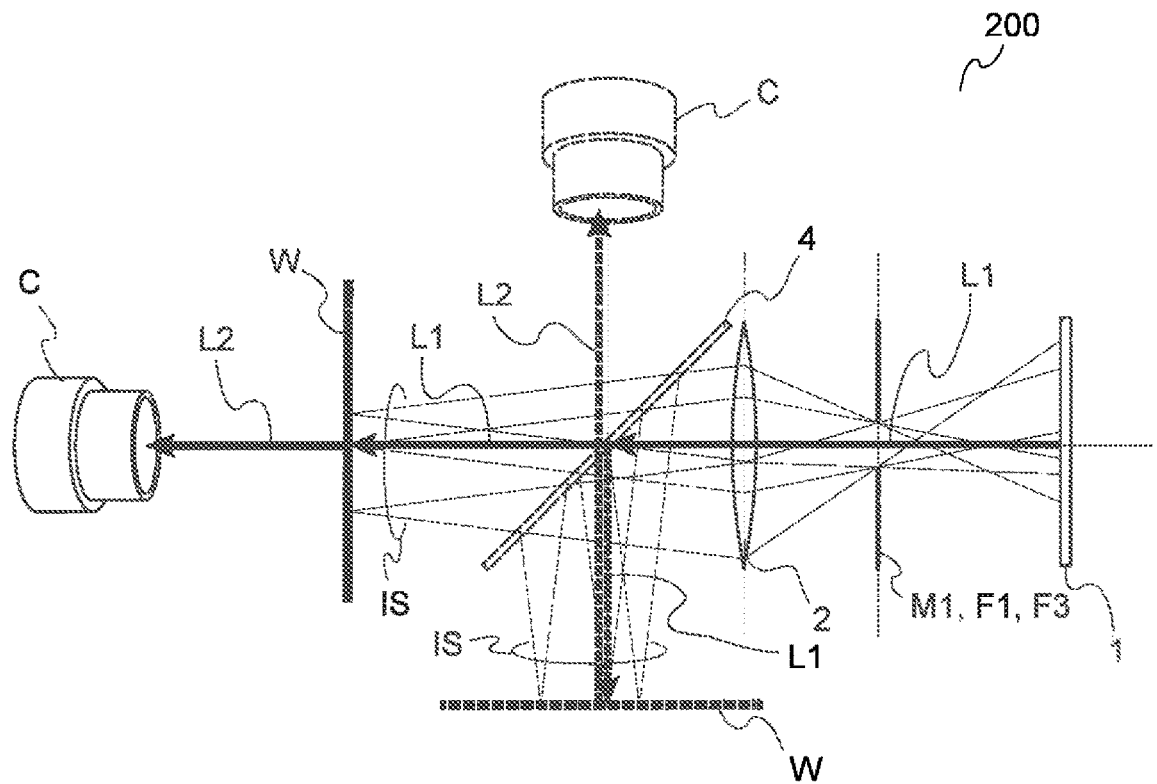

*1 Half mirror 4, imaging device C, inspection object W, and light path in the case where half mirror is provided are indicated by dashed lines.

*2 First shielding mask M1 denotes mask of shielding portion, F1 denotes portion, within aperture, that transmits only light having specific wavelength band or
polarization or that has specific transmittance, and F3 denotes irradiation solid angle forming means as a whole that integrates both. (see FIG. 4)

FIG. 3

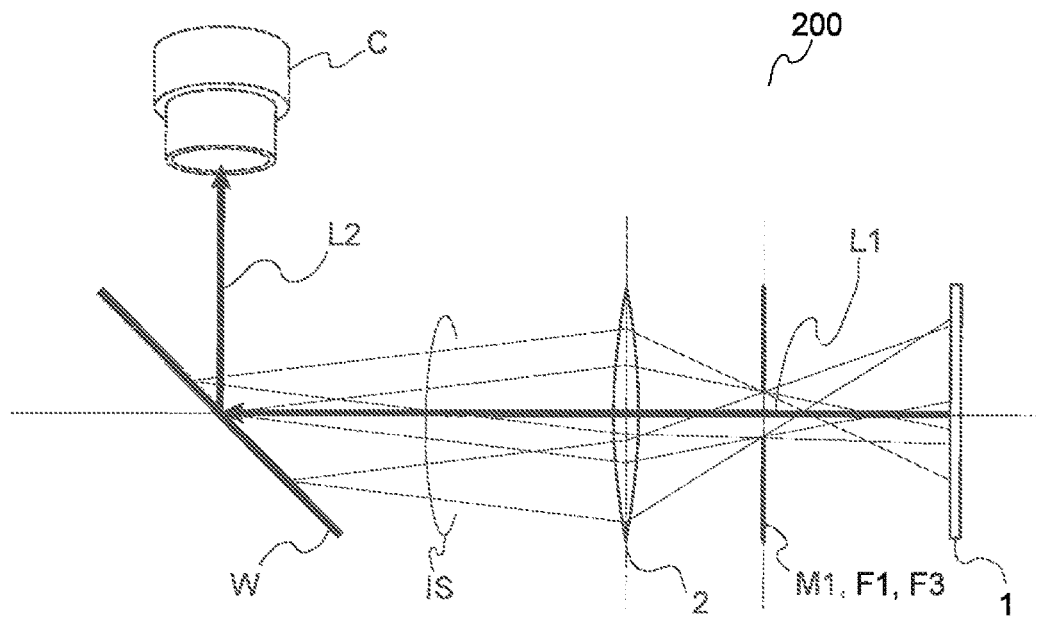

* First shielding mask M1 denotes mask of shielding portion, F1 denotes portion, within aperture, that transmits only light having specific wavelength band or polarization or that has specific transmittance, and F3 denotes irradiation solid angle forming means as a whole that integrates both. (see FIG. 4)

FIG. 4

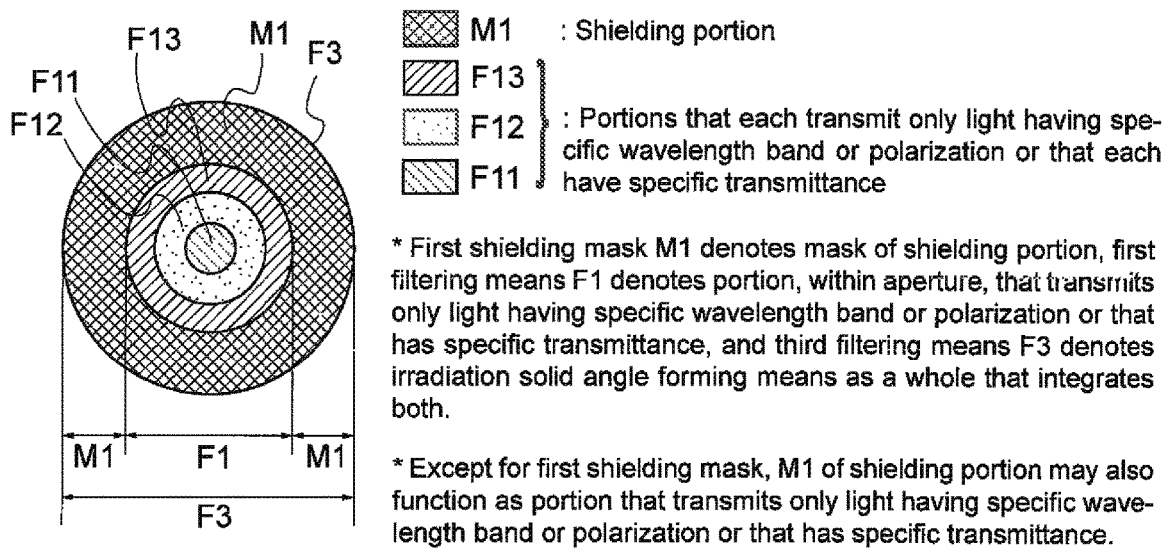

▨ M1 : Shielding portion

▨ F13 ⎫
▨ F12 ⎬ : Portions that each transmit only light having specific wavelength band or polarization or that each
▨ F11 ⎭ have specific transmittance

* First shielding mask M1 denotes mask of shielding portion, first filtering means F1 denotes portion, within aperture, that transmits only light having specific wavelength band or polarization or that has specific transmittance, and third filtering means F3 denotes irradiation solid angle forming means as a whole that integrates both.

* Except for first shielding mask, M1 of shielding portion may also function as portion that transmits only light having specific wavelength band or polarization or that has specific transmittance.

FIG. 5

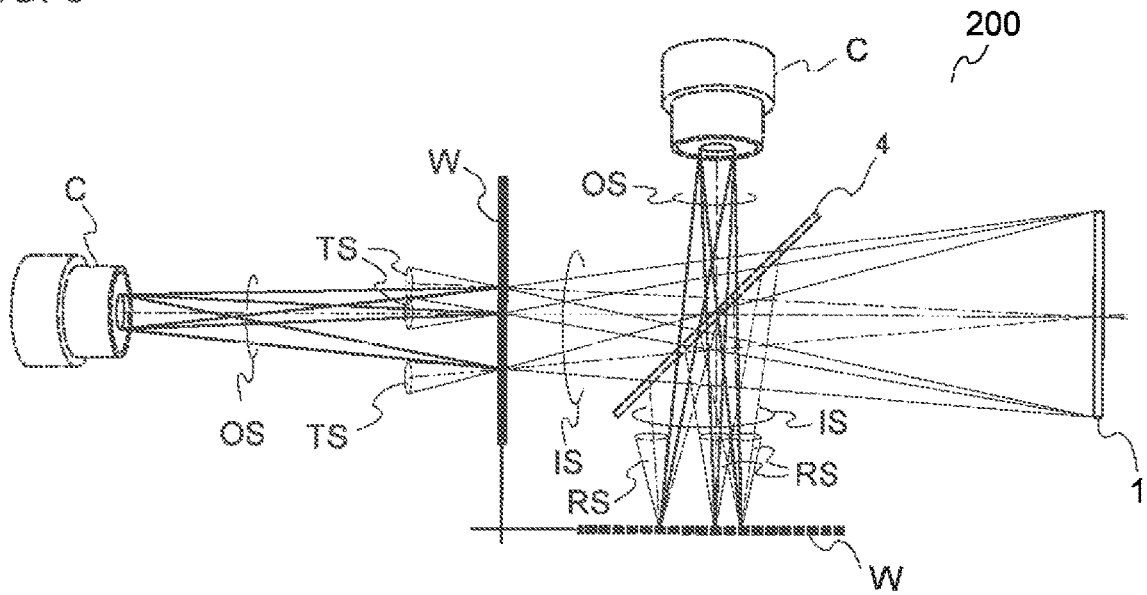

* Half mirror 4, imaging device C, inspection object W, and light path in the case where half mirror is provided are indicated by dashed lines, and observation solid angles are indicated by thick solid lines in either case.

FIG. 6

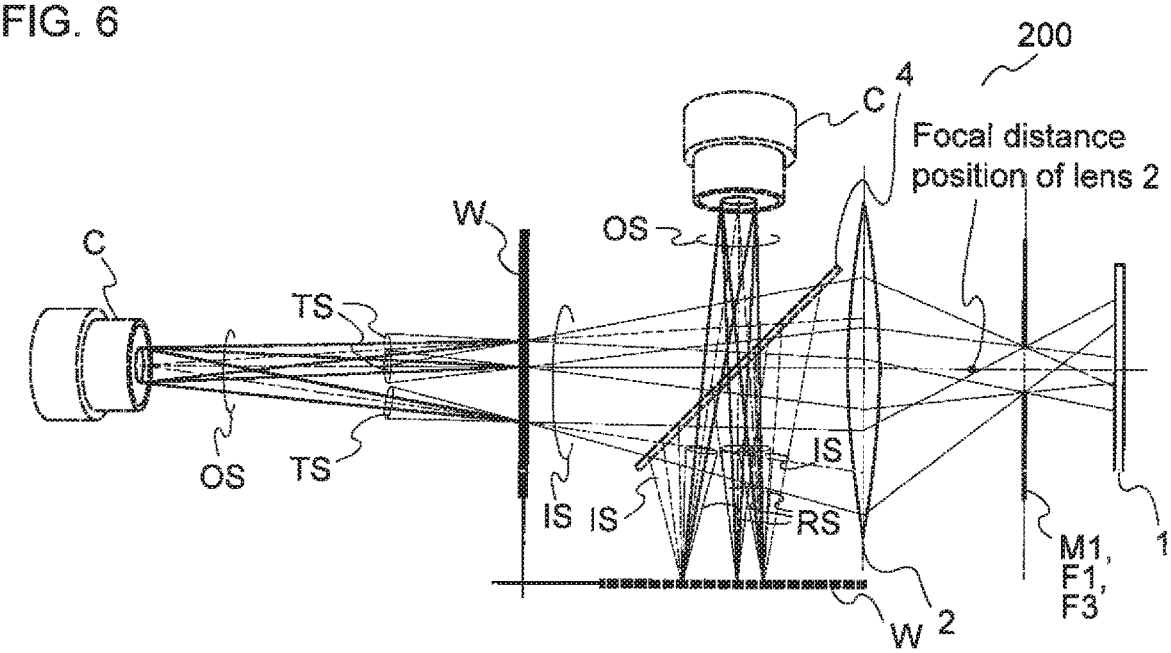

* Half mirror 4, imaging device C, inspection object W, and light path in the case where half mirror is provided are indicated by dashed lines, and observation solid angles are indicated by thick solid lines in either case.

FIG. 7

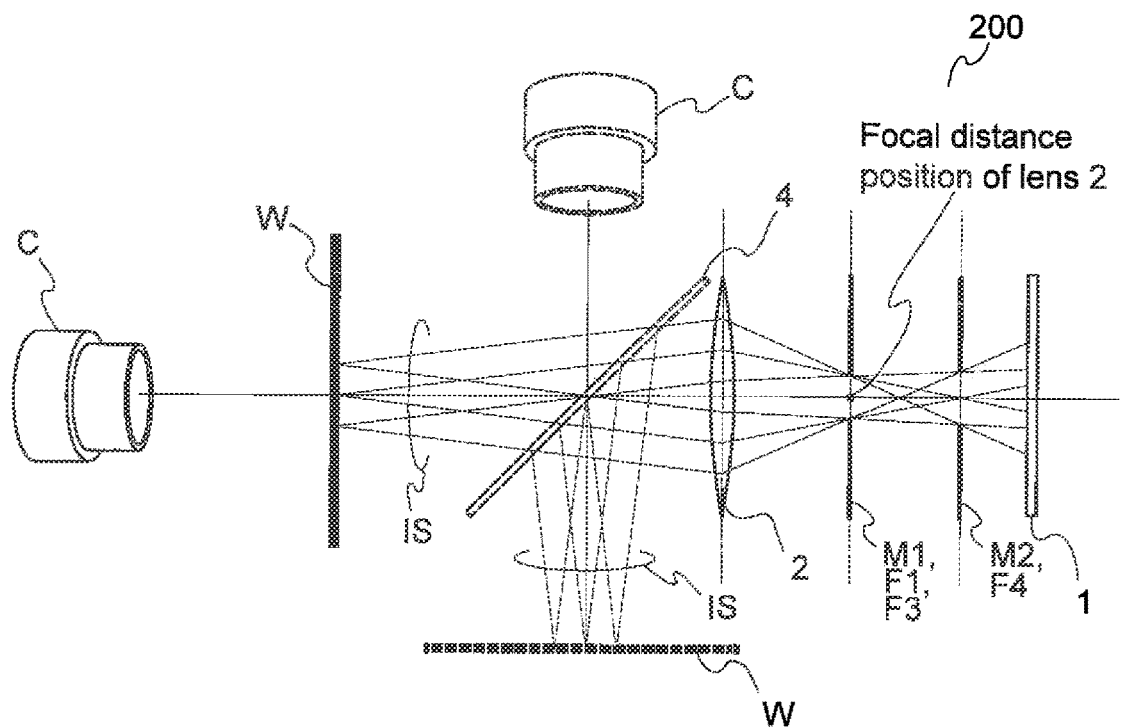

*1 Half mirror 4, imaging device C, inspection object W, and light path in the case where half mirror is provided are indicated by dashed lines.

*2 The distinction among M1, F1, and F3 is as follows: M1 denotes aperture in the diagram when regarded as aperture of shielding mask, F1 denotes aperture in the diagram when regarded as portion for specific wavelength band or polarization or having specific transmittance, and F3 denotes irradiation solid angle forming means as a whole that integrates both. (see FIG. 4)

*3 The distinction between M2 and F4 is as follows: M2 denotes aperture in the diagram when regarded as aperture of shielding mask, and F4 denotes aperture in the diagram when regarded as portion for specific wavelength band or polarization or having specific transmittance.

FIG. 8
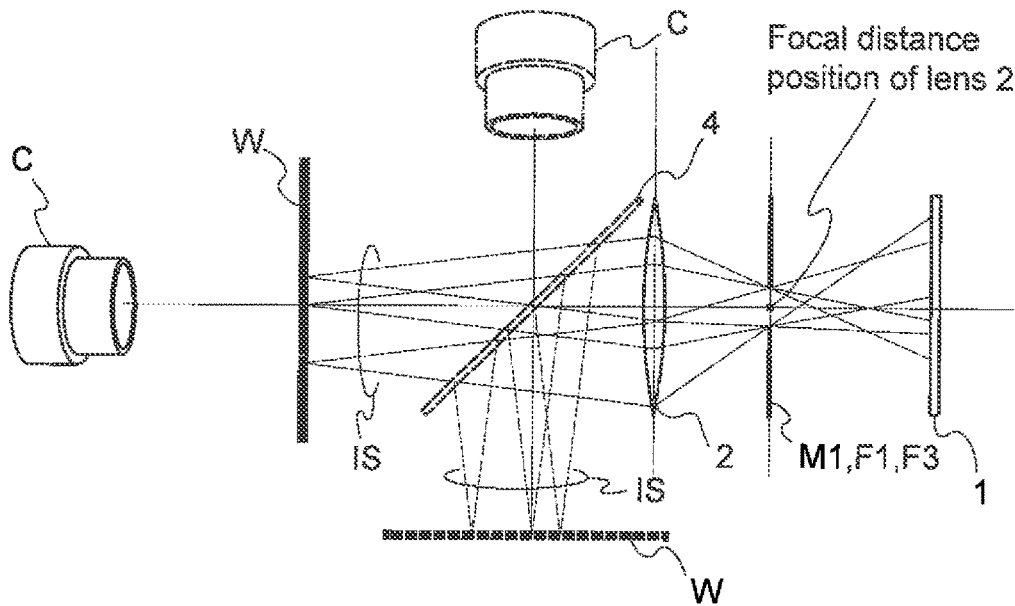
(a) When distance between inspection object and inspection lighting device is large
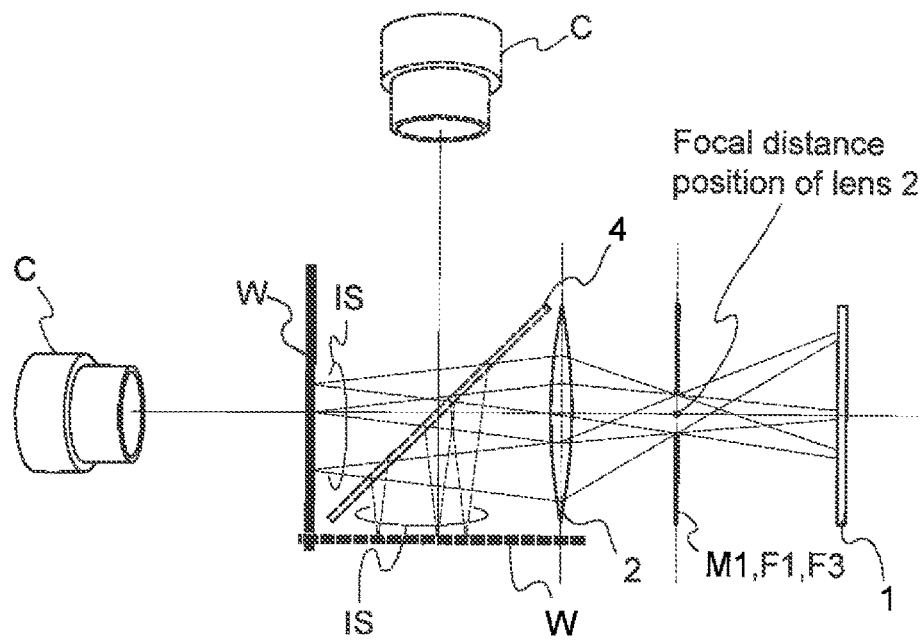
(b) When distance between inspection object and inspection lighting device is small
* Half mirror 4, imaging device C, inspection object W, and light path in the case where half mirror is provided are indicated by dashed lines.

FIG. 9

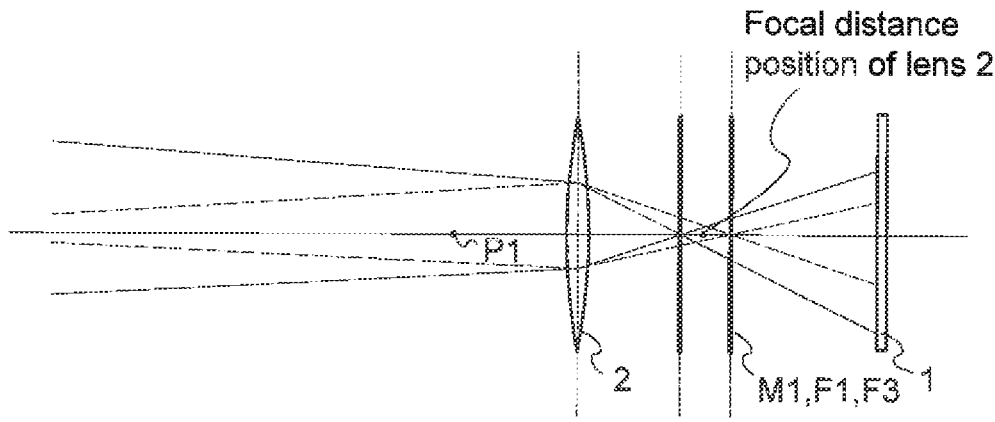

(a) When first shielding mask is extremely small transmitting portion and is located in the vicinity of focal distance position

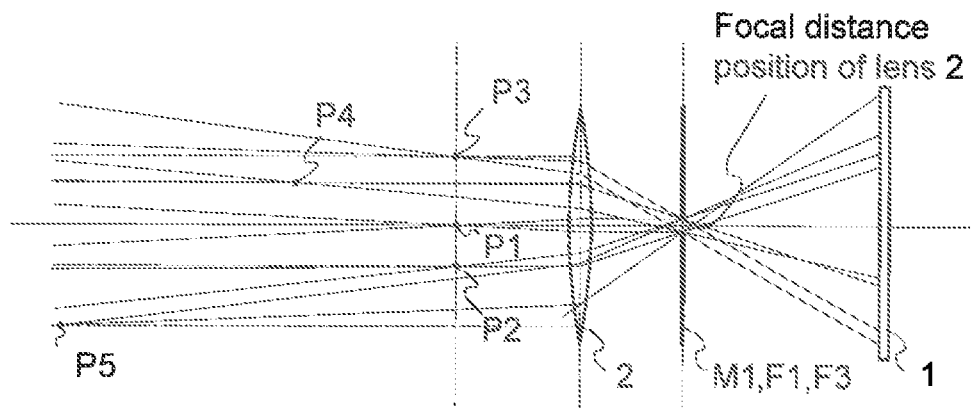

(b) When first shielding mask has a certain size and is located nearer to lens than focal distance position

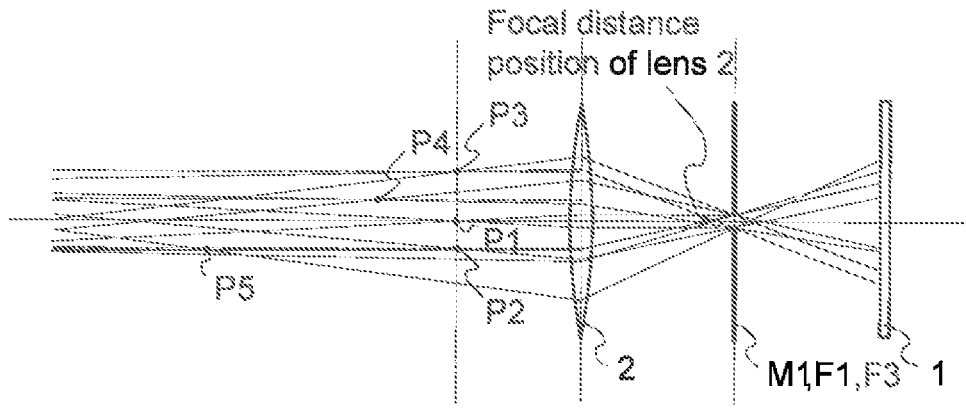

(c) When first shielding mask has a certain size and is located nearer to light source surface than focal distance position

*1 P1, P2, P3: Object-side focal distance position of lens 2

*2 P4, P5: Arbitrary point farther away than object-side P1 from lens 2

*3 Half plane angle of irradiation solid angle $\theta = tan^{-1}\left(\dfrac{r}{2f}\right)$ FIG. 10
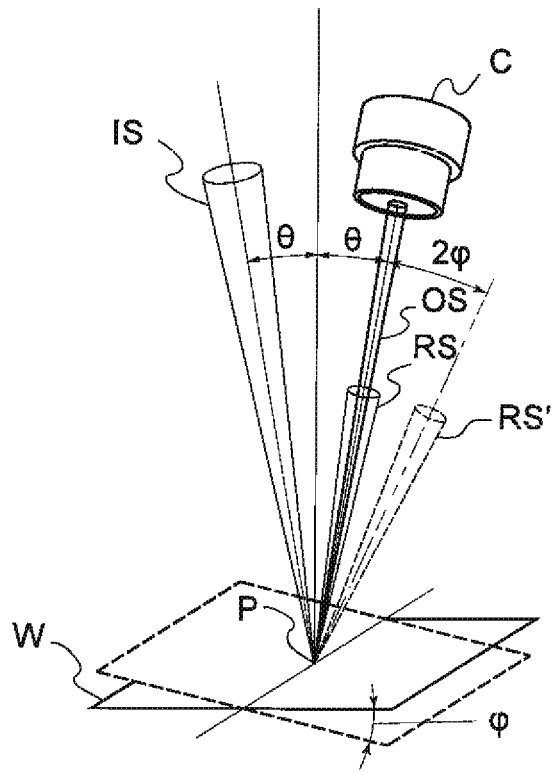
(a) Change in solid angle of reflected light due to partial inclination of inspection object
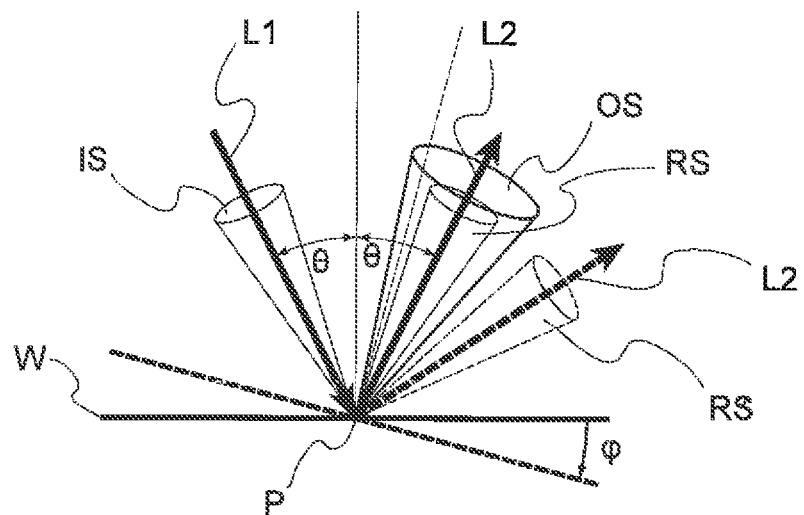
(b) Change in solid angle of reflected light and change in inclusive relation between solid angle of reflected light and observation solid angle FIG. 11
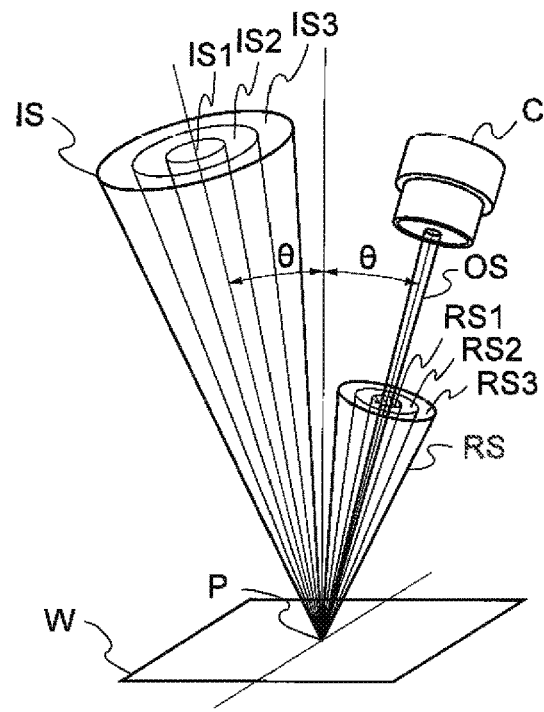
(a) When inspection surface is planar, optical axis of reflected light and optical axis of observation solid angle coincide with each other.
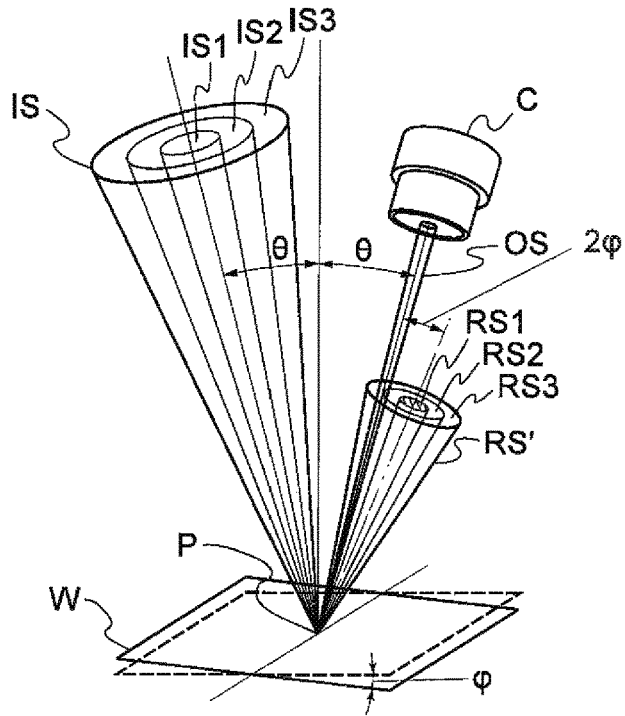
(b) When inspection surface is inclined, optical axis of reflected light is shifted from optical axis of observation solid angle.

FIG. 12
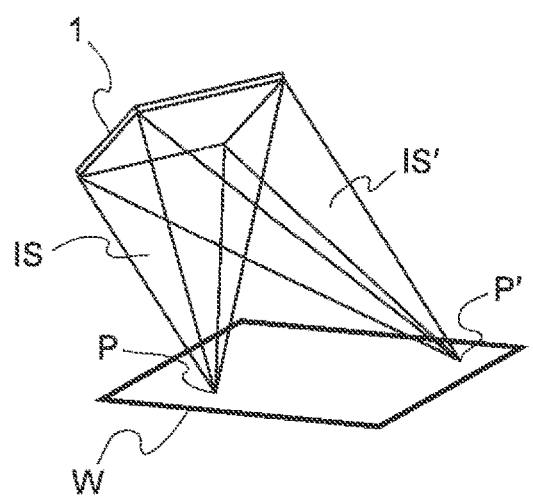 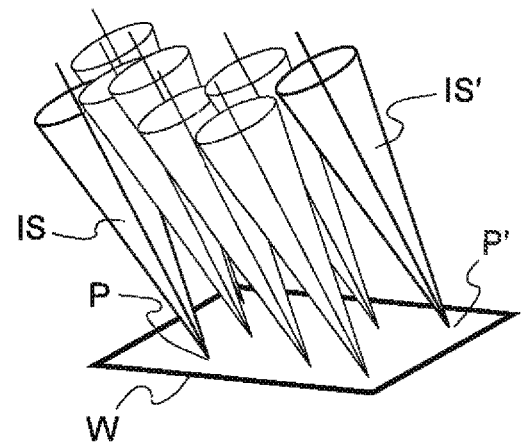
(a) Conventional lighting　　(b) Lighting of the present invention

… (1) …

LIGHTING DEVICE FOR INSPECTION AND INSPECTION SYSTEM

TECHNICAL FIELD

The present invention relates to a lighting device for inspection for use in inspecting an appearance, damage, a defect or the like of a product by, for example, irradiating inspection light onto a product which is an inspection object. The invention relates also to an inspection system.

BACKGROUND ART

As an example of an inspection lighting device for use in, for example, inspection of an appearance of a product, it is possible to cite a coaxial lighting device shown in Patent Document 1, in which an imaging direction is in agreement with a lighting direction for an inspection object. This coaxial lighting device includes a light source configured to emit inspection light in a direction parallel to an inspection object surface of the inspection object, and a half mirror disposed with an inclination between the inspection object and an imaging (image pick-up) device disposed upward of the inspection object and configured to reflect the inspection light toward the inspection object and to transmit the reflected light from the inspection object toward the imaging device.

Incidentally, in recent years, there is demand for the ability to detect a feature point such as a defect that is difficult to detect even with an inspection lighting device such as that described above through a captured image thereof. More particularly, there are cases where, since a product to be inspected does not have the surface characteristics of a perfect mirror surface, precision control of the optical axis and the shape and the like of an irradiation solid angle for obtaining desired gradation information regarding a feature point on the inspection object surface is difficult, and even if the inspection light can be irradiated, significant contrast variation may occur depending on the position on the inspection object at which the feature point is present, making it difficult to identify the feature point.

For example, it is conceivable to increase the inspection precision by limiting the irradiation area of the inspection light to only the inspection object with use of an aperture stop or the like and thereby decrease stray light which is reflected light or scattered light from a non-inspection target object.

However, even when reduction of such stray light coming into the imaging device is made possible with the above-described method, in the case of a very small defect or the like, significant variation occurs in the brightness of the captured image, which makes detection thereof as a defect impossible.

More specifically, even when a small change occurs in the reflection direction of the irradiated inspection light due to the presence of, for example, a small defect on the inspection object, if this change is in such a range as confined within an observation solid angle of the imaging device, the brightness of the captured image remains unchanged, regardless of the presence/absence of the defect, or if the irradiation solid angle of the inspection light is large and the inclination of its optical axis differs at different points on the inspection object, a small change in the reflection direction cannot be captured as a change in light amount within the observation solid angle of the imaging device; moreover, the light amount within the observation solid angle of the imaging device varies irregularly between the different points on the inspection object. Consequently, the machine vision is unable to accurately detect such small defects or the like in the inspection target area.

CITATION LIST

Patent Documents

Patent Document 1: JP 2010-261839A

SUMMARY OF INVENTION

Technical Problem

The present invention has been made in view of the above-described state of the art, and it is an object thereof to provide an inspection system and an inspection lighting device with which, even when a feature point such as a defect is extremely small or vague and causes only a slight change in reflection or scattering at that feature point, the light amount within an observation solid angle of an imaging device can change by a certain amount, and therefore, details of such a minute feature point can be detected, regardless of where the feature point, among the points on an inspection target within an imaging area, is in a field of view.

Solution to Problem

That is to say, the present invention has been made based on a novel technical concept that, with a configuration in which the forms, such as the sizes, shapes, and inclinations, of irradiation solid angles of inspection light emitted from an inspection lighting device can be made uniform, and, within each of the irradiation solid angles, the irradiation solid angle can be divided as desired, according to a factor of change in light other than the propagation direction, into, for example, regions having different wavelengths, polarization planes, light amounts, or the like, and what is more, this is adjustable, it is possible to capture even a slight amount of change in reflection or scattering caused by a minute defect or the like on an inspection object, within an observation solid angle of an imaging device, as changes in the light amount in the individual divided regions having different wavelength bands, polarization planes, or light amounts, and thus, an image containing the change as contrast information can be obtained.

More specifically, an inspection lighting device of the present invention is an inspection lighting device configured to irradiate inspection light onto an inspection object and to be applied to an inspection system constituted by the inspection lighting device and an imaging device for imaging light reflected, transmitted, or scattered by the inspection object, the inspection lighting device including: a surface light source configured for emitting inspection light; a lens disposed between the surface light source and the inspection object and configured to form on the inspection object an irradiation solid angle of light emitted from the surface light source and irradiated onto the inspection object as inspection light; and at least one of a first shielding mask and a first filtering means disposed between the surface light source and the lens and in front of or behind a focal distance position of the lens, centered around the focal distance position, the first shielding mask being configured to form an irradiation solid angle of the inspection light irradiated onto each point on the inspection object by shielding light, and the first filtering means being configured to divide the inspection light into solid angle regions as desired, the solid angle regions having partially different optical attributes for light having different wavelength bands, different polarization planes, or light having different light amounts, wherein, with respect to an observation solid angle that is formed at each point on the inspection object when the imaging device images light from the inspection object, a shape, a size, or an inclination of the irradiation solid angle as a whole and the solid angle regions having different optical attributes within the irradiation solid angle can be set as desired such that a desired change corresponding to the contrast of that point can be obtained for each of the solid angle regions having optical attributes, that is, having different wavelength bands, different polarization planes, or different light amounts. It should be noted that the first shielding mask and the first filtering means may also be integrated into a single third filtering means that has the functions of both thereof and that serves as a means for forming an irradiation solid angle having solid angle regions that can be set as desired.

Moreover, the inspection lighting device further includes at least one of a second shielding mask and a fourth filtering means, the fourth filtering means transmitting only light having a specific attribute, at a position between the surface light source and the first shielding mask and in the vicinity of a position at which the at least one of the second shielding mask and the fourth filtering means is imaged onto the inspection object by the lens, wherein an irradiation area or an irradiation pattern of the inspection light irradiated onto the inspection object can be generated as desired by using the second shielding mask or the fourth filtering means.

With the inspection system and the inspection lighting device described above, the lens and the first shielding mask or the first filtering means make it possible to form substantially uniform irradiation solid angles of inspection light irradiated onto the inspection object at respective points thereon and to form the above-described solid angle regions having different optical attributes, such as different wavelength bands or polarization planes, or light amounts, as desired, and furthermore, the lens and the second shielding mask or the fourth filtering means make it possible to irradiate the inspection light onto only a required portion of the inspection object or to form an irradiation area of the inspection light with a region having any desired optical attribute.

In other words, in the case where, for example, an ordinary lighting device having a surface light source or the like is used, the shape and the inclination of the irradiation solid angle at each point on the inspection object are determined by the relation between that point on the inspection object and the shape of the light source face of the lighting device, and therefore, it is difficult to obtain uniform inspection light. However, according to the present invention, while the shapes and the inclinations of irradiation solid angles at respective points on the inspection object can be made substantially uniform, and moreover, the inside of each irradiation solid angle can be divided into solid angle regions having different optical attributes, that is, having different wavelength bands or polarization planes, or light amounts, the form of irradiation of the irradiation solid angles can be adjusted. Furthermore, the inspection light can be irradiated onto only a required area, whereby stray light from the inspection object can be prevented.

In addition, in order that, even when a slight change in the intensity or the direction of reflected light, transmitted light, or scattered light occurs due to a minute defect or the like on the inspection object, a change in light amount corresponding to the portion where change occurs can be generated in each solid angle region with different optical attributes within an observation solid angle of the imaging device, the first shielding mask or the first filtering means makes it possible for the shape and the angle of the irradiation solid angle of the inspection light irradiated onto each point on the inspection object can be appropriately set in view of the relation thereof with the size, the shape, and the angle of the observation solid angle of the imaging device. Thus, the shape and the angle of irradiation solid angles can be appropriately set in accordance with the surface characteristics at feature points on on the object surface. Therefore, minute defects and the like can be easily detected, or conversely can be prevented from being detected.

Moreover, it is possible to form irradiation solid angles in various forms including, for example, a form in which, in an irradiation solid angle at each point on an inspection object, only the central portion constitutes a dark area, and only the peripheral portion constitutes a bright area. It is possible to image only scattered light by further forming solid angle regions having different optical attributes within an irradiation solid angle and thereby preventing reflected light and transmitted light from the inspection object from entering the observation solid angle of the imaging device. It is possible, based on the inclusive relation between the reflected light or the transmitted light and the observation solid angle, to observe a change in the propagation direction of the reflected light or the transmitted light on the inspection object as contrast information regarding to each point on the inspection object. Furthermore, when the imaging device includes a second filtering means that enables selective imaging of the solid angle regions having different optical attributes within an irradiation solid angle that are reflected in the solid angle of the reflected light or the transmitted light, it is possible to capture a change that occurs at a feature point on the inspection object for each of the solid angle regions that are set as desired. Thus, inspection light can be irradiated at irradiation solid angles in appropriate forms that are suited to various inspection objects or minute changes in light that occur at various feature points to be detected.

To realize the second filtering means herein, in the imaging device, for example, a configuration may be adopted in which the reflected light or the transmitted light from the inspection object is selectively dispersed for each of the different optical attributes, and then the resultant light amounts are individually imaged by an optical sensor, or another configuration may be adopted in which a filter that selectively transmits only light having a distinct optical attribute, of the different optical attributes, may be provided for each pixel of the optical sensor.

In the case where inspection light having substantially uniform irradiation solid angles according to the present invention is irradiated onto the inspection object, in order to enable capturing of even a slight change in the solid angle of reflected light or transmitted light that occurs when the reflection direction or the transmission direction is changed due to a defect or the like, the relation between the irradiation solid angle of the inspection light at the point of that change and the observation solid angle of the imaging device can be adjusted with respect to the shapes, angles, and sizes thereof such that a change in light amount within the observation solid angle corresponding to the change in the solid angle is maximized, and any other changes are minimized. Thus, only the change in the solid angle of the reflected light or the transmitted light can be selectively captured. Moreover, if any desired solid angle regions having different optical attributes are further set within the irradiation solid angle, changes in light amount in the respective solid angle regions can be observed simultaneously, so that changes in light corresponding to changes in light at various feature points on the inspection object can be continuously captured. Accordingly, although it is difficult for a conventional lighting device, with which the shape, angle, and size of irradiation solid angles of inspection light differ at different points on the inspection object surface, to capture a slight change in light caused by a minute defect or the like as described above, the lighting device according to the present invention enables capturing of such a slight change.

In order to control the sizes of irradiation solid angles of inspection light irradiated onto respective points on the inspection object so as to be substantially uniform, and to enable adjustment of the inclination distribution of the irradiation solid angles with respect to the center of the optical axis, the first shielding mask and the first filtering means, or the third filtering means that integrates the functions of both, can be disposed at a position in front of or behind the focal distance position of the lens, centered around the focal distance position. In the following description, the first shielding mask, the first filtering means, and the third filtering means are represented by the first shielding mask. That is to say, irradiation solid angles at respective points on the inspection object can each be set to have a desired shape or size by changing the aperture of the first shielding mask. Also, if the first shielding mask is disposed at the focal distance position of the lens, all of the optical axes of the irradiation solid angles of the inspection light become parallel to the optical axis of the inspection light; if the first shielding mask is disposed nearer to the lens than the focal distance position of the lens, the irradiation solid angles of the inspection light can be inclined in a direction in which the inspection light widens; and if the first shielding mask is disposed outward of the focal distance position of the lens, the irradiation solid angles of the inspection light can be inclined in a direction in which the inspection light narrows. As described above, irradiation solid angles of the inspection light that have a direct effect on the solid angle of reflected light or transmitted light from the inspection object can be adjusted in various manners by changing the position and the aperture of the first shielding mask, and thus, the relation between the inspection object and the observation solid angle of the imaging device for observing reflected light, transmitted light, or scattered light from the inspection object can be optimized to obtain desired contrast information. That is to say, with the above-described configuration, even when an observation optical system that is used is not a telecentric optical system but rather an optical system in which the inclination of the optical axis of the observation solid angle varies between the outside of the field-of-view range and the center of the optical axis, for all points across the entire field of view, the irradiation solid angle and the observation solid angle can be set in a regular reflection direction.

Furthermore, with regard to the above-described solid angle regions having different optical attributes, which are set as desired within an irradiation solid angle, solid angle regions can further be set as desired within each of the irradiation solid angles that are set to be uniform on the inspection object. Thus, not only the brightness at each point on the inspection object is determined simply by the relation between the irradiation solid angle and the observation solid angle, but also even slighter changes in light in the individual solid angle regions can be observed simultaneously as changes in the relation with the observation solid angle under substantially the same conditions for all the points in the field-of-view range on the inspection object, without the need to separately reset the relation between the irradiation solid angle and the observation solid angle with respect to their shapes, optical axes, and the like.

Therefore, in the inspection lighting device according to the present invention, and the inspection system that uses the inspection lighting device and that also includes an imaging device for imaging light reflected, transmitted, or scattered by the inspection object, desired contrast information with respect to a minute feature point can be obtained for the following reasons. Given that the contrast at each point on the inspection object is determined by the light amount of reflected light, transmitted light, or scattered light toward the imaging device from that point on the inspection object, and the light amount is in turn determined by the inclusive relation between the solid angle of the reflected light, transmitted light, or scattered light from that point on the inspection object and the observation solid angle of the imaging device, the inspection lighting device and hence the inspection system have the function of adjusting irradiation solid angles, which have a direct effect on reflected light or transmitted light from respective points on the inspection object, of the inspection light so as to be substantially uniform, and furthermore, the inside of each irradiation solid angle is divided into any desired solid angle regions having different wavelength bands or polarization planes, or light amounts, so that the imaging device can selectively observe the light amount for each divided region.

In order that contrast information regarding the inspection object that is imaged by the imaging device exhibits substantially uniform changes across the entire imaging area, the inclusive relations between the observation solid angles that are formed at respective points on the inspection object by the imaging device and the solid angles of reflected light, transmitted light, or scattered light from the respective points on the inspection object have to be kept substantially uniform. This can be realized by moving the first shielding mask and the first filtering means, or the third filtering means, to a position in front of or behind the focal distance position of the lens, centered around the focal distance position, thereby adjusting the shapes and sizes of irradiation solid angles of the inspection light and solid angle regions formed within the individual irradiation solid angles so as to be substantially uniform and also adjusting the inclination angles so as to be included in the inclinations of the observation solid angles at the respective points on the inspection object.

Also, in order to make it possible to generate an irradiation area, an irradiation shape, or an irradiation pattern as desired while keeping substantially uniform relations between irradiation solid angles of the inspection light incident on the inspection object and solid angle regions that are formed as desired within each irradiation solid angle with observation solid angles for respective points within the irradiation area, in addition to the at least one of the first shielding mask and the first filtering means, or the third filtering means, at least one of the second shielding mask and the fourth filtering means can be provided and disposed in the vicinity of a position at which the at least one of the second shielding mask and the fourth filtering means is imaged onto the inspection object by the lens. With this configuration, while keeping substantially uniform shapes, sizes, and inclinations of the irradiation solid angles of the inspection light and the solid angle regions that are formed as desired within the irradiation solid angles, it is possible to independently adjust both the irradiation area of the inspection light on the inspection object and the optical attributes of that irradiation area as well as the irradiation solid angles of the inspection light at respective points on the inspection object and the solid angle regions having specific optical attributes.

In order to make it possible to easily inspect the three-dimensional shape and the like of the inspection object as well, in addition to the first shielding mask and first filtering means, or the third filtering means, the second shielding mask in which a predetermined mask pattern is formed and the fourth filtering means can be used, and the pattern can be imaged onto the inspection object. With this configuration, due to substantially uniform irradiation solid angles and solid angle regions having specific optical attributes, which are adjusted by using the first shielding mask and the first filtering means, the imaging device can obtain contrast information that exhibits uniform changes in contrast, and if there is any problem with the shape of the inspection object, distortion occurs in the pattern that is obtained as the contrast information by the imaging device, so that the defect in shape can be easily detected.

If the shape, size, and inclination of the solid angle of reflected light or transmitted light at each point on the inspection object are made to substantially coincide with those of the observation solid angle that is formed at that point on the inspection object by the imaging device, even a minute feature point that is present on the inspection object, if any, results in a change in the inclusive relation between the solid angle of the reflected light or the transmitted light and the observation solid angle, so that a change in contrast information with respect to that minute feature point can be obtained. The rate of change in contrast information based on a change in the inclusive relation can be controlled by appropriately setting the sizes of the solid angle of the reflected light or the transmitted light and the observation solid angle. However, without any further processing, merely limited contrast information that depends on the size of the two solid angles can be obtained. To address this issue, solid angle regions having different wavelength bands, polarization planes, or light amounts are formed as desired within the irradiation solid angle at each point on the inspection object. Then, those solid angle regions are reflected in the solid angle of the reflected light or the transmitted light at that point on the inspection object as solid angle regions having different wavelength bands, polarization planes, or light amounts. Thus, if a change in contrast information with respect to a feature point is based on the inclusive relations between the observation solid angle and the solid angle regions that are reflected in the solid angle of the reflected light or the transmitted light, minute amounts of change in the respective solid angle regions can be detected simultaneously.

This can be realized by two approaches: one of these approaches is a configuration in which a half mirror for changing the irradiation direction of the inspection light and transmitting light from the inspection object so as to be imaged by the imaging device is provided, and an optical axis of an observation solid angle of the imaging device at each point on the inspection object and an optical axis of a solid angle of the reflected light or the transmitted light emitted from that point are made to substantially coincide with each other by appropriately adjusting an irradiation solid angle of the inspection light at that point on the inspection object, and the other approach is a configuration in which an observation solid angle of the imaging device is set in a direction that is line symmetrical to the irradiation direction of the inspection light with respect to a normal line to the inspection object, and the optical axis of the solid angle of the reflected light or the transmitted light from each point on the inspection object and the optical axis of an observation solid angle of the imaging device at that point on the inspection object are made to substantially coincide with each other.

Furthermore, if the imaging device includes the second filtering means, which enables selective imaging of light in solid angle regions that are reflected in the solid angle of the reflected light or the transmitted light and that have different wavelength bands, polarization planes, or light amounts, possible changes in contrast that may occur based on the inclusive relations of the individual solid angle regions with the observation solid angle can be detected simultaneously.

Advantageous Effects of Invention

As described above, according to the inspection lighting device and the inspection system of the present invention, it is possible to freely adjust the sizes and forms of irradiation solid angles of inspection light irradiated onto respective points on an inspection object and dark areas thereof as well as solid angle regions that are formed within each irradiation solid angle and that have different wavelength bands, polarization planes, or light amounts. Thus, inclusive relations of solid angles of reflected light, transmitted light, or scattered light from respective points on the inspection object and solid angle regions that have different wavelength bands, polarization planes, or light amounts and that are reflected in those solid angles with observation solid angles that are formed at the respective points on the inspection object by the imaging device can be set to be substantially uniform. Therefore, even minute defects and the like that have conventionally been difficult to detect can be detected under substantially the same conditions.

BRIEF DESCRIPTION OF DRAWINGS

FIG. 1 is a schematic perspective view showing an appearance of an inspection lighting device and an inspection system according to an embodiment of the present invention.

FIG. 2 is a diagram schematically showing an inner structure of a main portion for forming an irradiation solid angle of the inspection lighting device and the inspection system of the embodiment, and irradiation solid angles at respective points on an inspection object.

FIG. 3 is a diagram schematically showing the inner structure of the main portion for forming an irradiation solid angle of the inspection lighting device and the inspection system of the embodiment, with the inspection object being placed inclined, also showing irradiation solid angles at respective points on the inspection object.

FIG. 4 shows a configuration example of a first shielding mask and a first filtering means as well as a third filtering means.

FIG. 5 is a diagram schematically showing a structure of an inspection lighting device and an inspection system for conventional lighting use, and irradiation solid angles at respective points on an inspection object.

FIG. 6 is a diagram schematically showing a structure of a main portion for forming an irradiation solid angle of an inspection lighting device and an inspection system according to an embodiment of the present invention, and irradiation solid angles at respective points on an inspection object.

FIG. 7 is a diagram schematically showing a structure of an inspection lighting device and an inspection system according to an embodiment in which a second shielding mask and a fourth filtering means are additionally provided, and irradiation solid angles at respective points on an inspection object.

FIG. 8 schematically shows a main portion for forming an irradiation solid angle of an inspection lighting device according to an embodiment of the present invention, and irradiation solid angles at respective points on an inspection object, with the distance from the inspection object of an inspection system being used as a parameter.

FIG. 9 schematically shows irradiation solid angles at respective points on an inspection object, with the size of an aperture of the first shielding mask of an inspection lighting device and an inspection system according to an embodiment of the present invention being used as a parameter.

FIG. 10 shows relations of a change in solid angle of reflected light due to a partial inclination of the inspection object with an irradiation solid angle and an observation solid angle.

FIG. 11 shows relations of a change in solid angle of reflected light due to a partial inclination of the inspection object with an irradiation solid angle and an observation solid angle when the irradiation solid angle contains solid angle regions having different optical attributes.

FIG. 12 shows a comparison between conventional lighting and lighting according to the present invention in terms of irradiation solid angles.

DESCRIPTION OF EMBODIMENTS

Figure 13:
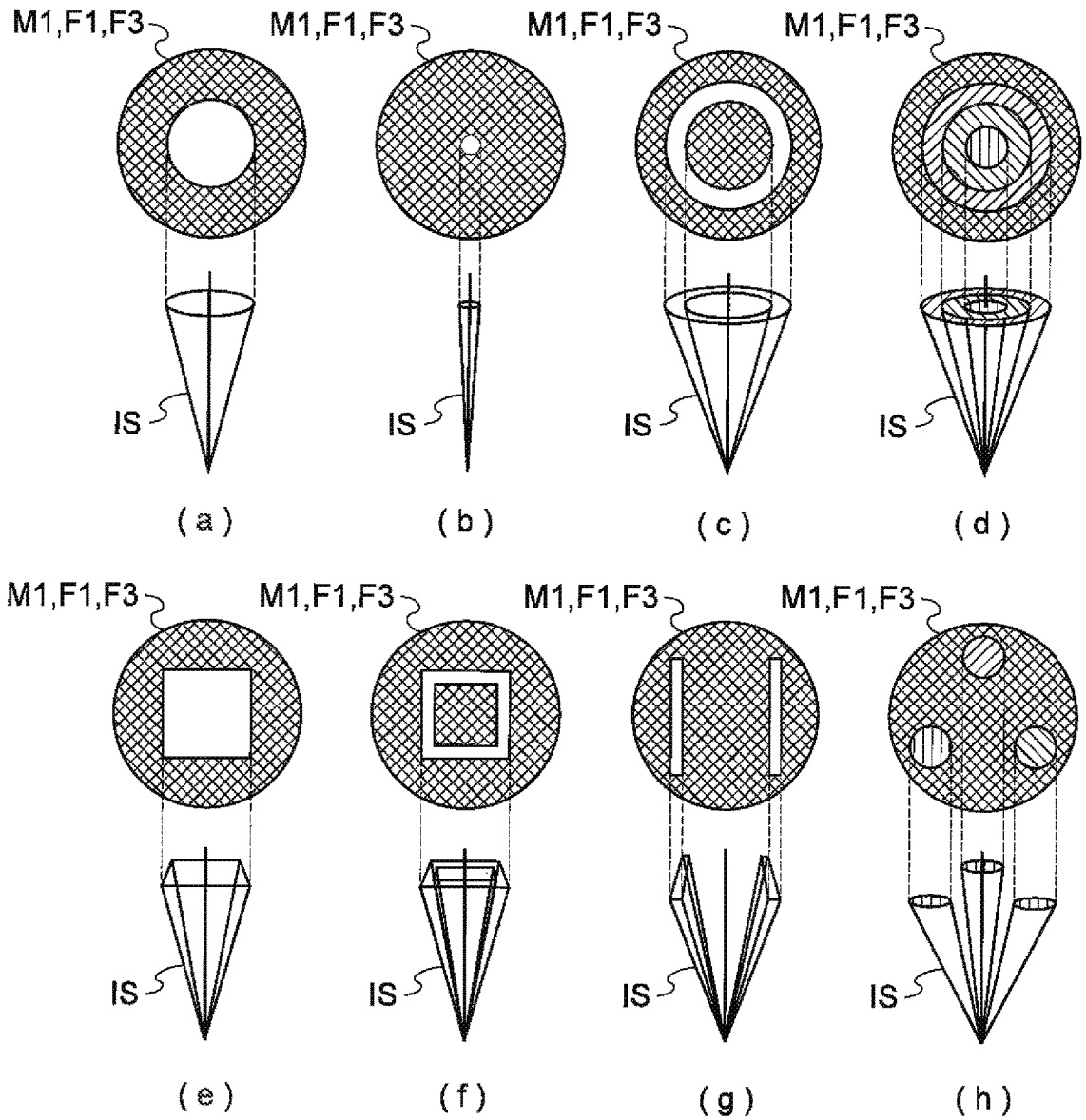
FIG. 13 shows examples of the shape of the irradiation solid angle that may be set according to the present invention.

A first embodiment of the present invention will be described.

An inspection system 200 constituted by an inspection lighting device 100 of the first embodiment and an imaging device C is configured to provide a so-called coaxial lighting arrangement using a half mirror 4 for providing agreement between an imaging direction of an inspection object W and a lighting direction of the inspection object W, and is used to cause a feature point such as a defect that is present on the inspection object W to appear as a contrast in an image captured by the imaging device C. It should be noted that, in FIGS. 2 and 5 through 8, a case with a half mirror is indicated by dotted lines, whereas a case without a half mirror is indicated by solid lines. Moreover, a first filter F1 serves as a means for selectively transmitting light having a specific attribute and forming a solid angle region composed of the light having that attribute. In terms of the effect of forming a solid angle, the first filter F1 is equivalent to a first shielding mask M1, which forms an irradiation solid angle by shielding or transmitting light. Thus, in FIGS. 1 to 3 and 6 to 9, the first filter F1 and the first shielding mask M1, as well as a third filtering means F3, which is a single component into which the functions of both the first filter F1 and the first shielding mask M1 are integrated, are represented by the first shielding mask M1, and only the reference numerals F1 and F3 are shown along with M1. Here, the "feature point" such as a defect on the inspection object W is to be understood to include a broad range of defects such as a scratch, a dent, a distortion on the surface, a defect in the external shape, and the presence/absence of a hole and other types of features.

As shown in the perspective view of FIG. 1 and the schematic diagram of FIG. 2, the inspection lighting device 100 has a substantially tubular housing. Inside this housing and in portions leading to the inspection object W and the imaging device C, there are formed an irradiation light path L1 for irradiating an inspection light from a surface light source 1 onto the inspection object W, and a reflection/transmission light path L2 along which light reflected or transmitted by the inspection object W travels to the imaging device C. In the case where the half mirror 4 is provided, the imaging device C is mounted to a top opening side of the housing, and the inspection object W is placed on a bottom opening side of the housing.

It should be noted that, as shown in FIGS. 1 and 2, in the case where the half mirror 4 is provided, the irradiation light path L1 is constituted by a portion extending from the surface light source 1 to the half mirror 4 and a portion along which the light partially reflected by the half mirror reaches the inspection object. On the other hand, in the case where the half mirror 4 is not provided, the inspection light is directly irradiated onto the inspection object along the irradiation light path L1, and in the example shown in FIG. 2, a light path along which transmitted light from the inspection object W reaches the imaging device C constitutes the light path L2.

On the irradiation light path L1, in the order of traveling of the inspection light, there are disposed the surface light source 1 for emitting the inspection light, at least one of the first shielding mask M1 and the first filtering means disposed at a position in front of or behind a focal distance position of a lens 2, centered around the focal distance position, or instead, the third filtering means F3 having the functions of both the first shielding mask M1 and the first filtering means, and the lens 2 configured to form an irradiation solid angle for the inspection object W from the inspection light emitted from the surface light source 1. In the case where a half mirror is provided, in addition to the above components, the half mirror 4 is disposed inclined relative to the reflection/transmission light path L2 and the irradiation light path L1 so as to partially reflect the inspection light downwards. Moreover, in the case where a second shielding mask and a fourth filtering means for forming an irradiation area of the inspection light are provided, at least one of the second shielding mask M2 and the fourth filtering means for forming an irradiation area having a specific optical attribute is provided between the surface light source 1 and the first shielding mask and the first filtering means, or between the surface light source 1 and the third filtering means, and in the vicinity of the position at which the second shielding mask M2 and/or the fourth filtering means is imaged onto the inspection object W by the lens 2, and the inspection light is irradiated onto the inspection object W. Specific functions provided by the second shielding mask if provided will be described later with reference to FIG. 7.

Moreover, in the case where a half mirror is provided, the half mirror 4 is provided on the reflection/transmission light path L2, so that the reflected light partially transmitted by this half mirror 4 is observed by the imaging device C. In the case where no half mirror is provided, in the example shown in FIG. 2, the light path along which the light transmitted from the inspection object W travels to reach the imaging device C constitutes the light path L2. No other component than the half mirror 4 is present on the light path L2 in FIGS. 1 and 2; however, depending on the circumstances, a mask, an aperture stop, or the like for partially shielding the reflected or transmitted light from the inspection object may also be provided on the light path L2 for the purpose of shutting out stray light from the inspection object.

Next, layouts, arrangements, and functions of the various members will be described in detail.

The surface light source 1 has a light-emitting face 11 that has a substantially uniform diffuser face formed by a chip type LED, a diffusion plate or the like, for example. Moreover, as shown in FIG. 1, the surface light source 1 is mounted in such a manner that it can advance or retract in the direction of the optical axis of the irradiation light inside the tubular housing so as to enable adjustment of the irradiation starting position for the inspection light. In this manner, independent of control of irradiation solid angles and solid angle regions having different optical attributes that are formed as desired within the irradiation solid angles by the first shielding mask M1 and the first filtering means F1, or the third filtering means F3 having the functions of both thereof, and control of the irradiation area by the second shielding mask, which will be described later, it is possible to control the degree of uniformity, the luminance distribution, and the like of the inspection light on the inspection object W, with respect to the light path of the inspection light that is determined by the positional relations among the first shielding mask M1 and the first filtering means F1, or the third filtering means F3 having the functions of both thereof, the second shielding mask M2, the lens 2, and the surface light source 1. Since the irradiation light path differs depending on the irradiation area, if, for example, the surface light source 1 is preset with a predetermined luminance distribution, emission light wavelength distribution, polarization characteristics distribution, or the like, such distribution can be changed or can be made uniform, depending on the irradiation area.

As shown in FIG. 1, the second shielding mask M2 and the fourth filtering means are mounted in such a manner that they can advance or retract in the direction of the optical axis of the irradiation light inside the tubular housing, so that, in accordance with the distance between the lens 2 and the inspection object, the second shielding mask itself can be adjusted to be in the vicinity of a position at which it is imaged onto the inspection object. With this arrangement, as shown in FIG. 7, the irradiation light from the surface light source 1 can be partially shielded, or only light having a specific attribute can be shielded, and the shape of the aperture of the second shielding mask or the shape of a portion of the fourth filter that transmits only light having a specific attribute is substantially imaged onto the inspection object W. Thus, by changing the shape and size of the aperture of the second shielding mask M2 or the pattern shape of the fourth filtering means, the irradiation area of the inspection light or the irradiation area to be irradiated with light having a specific attribute, on the inspection object W, can be set as desired. Moreover, this adjustment or setting can be carried out independently of the control of the irradiation solid angle by the first shielding mask M1 and the first filtering means F1, or the third filtering means F3 having the functions of both thereof, which will be described later.

The first shielding mask M1 and the first filtering means F1, or the third filtering means F3, which has the functions of both thereof, are disposed at a position between the lens 2 and the surface light source and in front of or behind the focal distance position of the lens 2, centered around the focal distance position, and are mounted such that they can advance and retract in the direction of the optical axis of the irradiation light inside the tubular housing as shown in FIG. 1. Here, taking the first shielding mask M1 as a representative example of the first shielding mask M1 and the first filtering means F1 as well as the third filtering means F3, which has the functions of both thereof, if the first shielding mask M1 is disposed at the focal distance position of the lens 2, for example, all irradiation solid angles IS at respective points on the inspection object W have the same size, shape, and inclination angle as shown in FIG. 2. The same holds true for the case where the points on the inspection object are at different distances from the lens 2 as shown in FIG. 3. Moreover, as shown in FIG. 8, the same holds true regardless of the presence or absence of the half mirror 4 and regardless of the distance between the inspection object W and the lens 2. The foregoing description that has been given taking the first shielding mask M1 as a representative example also applies to the solid angle regions that are formed by the first filtering means F1 and the third filtering means F3, which has the functions of both the first shielding mask M1 and the first filtering means F1.

Next, a case where the first shielding mask M1 and the first filtering means F1, or the third filtering means F3, which has the functions of both thereof, are located in front of or behind the focal distance position of the lens 2 will be described taking the first filtering means F1 as a representative example.

As shown in FIG. 9(*a*), first, when the first shielding mask M1 is located in the vicinity of the focal distance position with an extremely small transmitting portion, irradiation solid angles are approximately 0, when the first shielding mask M1 is located nearer to the lens 2 than the focal distance position of the lens 2, the light path of the inspection light is inclined so as to flare out gradually from the center of the optical axis as indicated by the solid lines in FIG. 9(*a*), and when the first shielding mask M1 is located nearer to the surface light source 1 than the focal distance position of the lens 2, the light path of the inspection light is inclined so as to converge at the center of the optical axis as indicated by the dashed lines in FIG. 9(*a*). On the other hand, the shapes and sizes of the irradiation solid angles of the inspection light at respective points on the inspection object are uniformly determined by the shape and size of the aperture of the first shielding mask M1 as shown in FIGS. 9(*b*) and 9(*c*). Independent of this, the inclinations of the irradiation solid angles can be controlled by controlling the position of the first shielding mask M1.

P1, P2, and P3 in FIG. 9 denote respective points at distances indicating the object-side focal distance positions of the lens 2. Only light that is directed by the lens 2 to travel along a light path that is parallel to the optical axis of the light irradiated from the surface light source 1 passes through at least the point P1. If the aperture of this light path that is determined by the first shielding mask M1 has a diameter "r", for example, the irradiation solid angle at the point P1 is uniquely determined by only the focal length "f" of the lens 2 and the diameter "r" of the aperture, as shown at the bottom in FIG. 9. Ideally, the same holds true for the points P2 and P3, which are located at the same distance from the lens as the point P1. Moreover, at arbitrary points P4 and P5 that are located farther than the focal length of the lens 2 as well, all of the irradiation solid angles ideally have the same shape and the same size as the irradiation solid angle at the point P1.

With regard to the first shielding mask M1, the first filtering means F1, and the third filtering means F3, as shown in FIG. 4, for example, a shielding portion M1 that substantially shields light forms an aperture having any desired shape. Although an example in which a peripheral portion constitutes the shielding portion and a central portion constitutes the aperture is shown in FIG. 4, a portion of the aperture may further constitute a shielding portion. Moreover, the shielding portion may also be a portion that shields only light having a specific attribute. Furthermore, in FIG. 4, the first filtering means F1 is set within the aperture of the shielding portion M1, and here, three types of patterns F11, F12, and F13 for forming respective solid angle regions with different optical attributes are set therein. Although the patterns shown here are concentric, the patterns may also be optimized to any pattern in accordance with a feature point of interest on the inspection object. A single component into which the first shielding mask M1 and the first filtering means F1 are integrated corresponds to the third filtering means F3.

With use of the first shielding mask M1 and the first filtering means F1, or the third filtering means F3, which are shown in FIG. 4, an irradiation solid angle IS can be formed with respect to a single point P on the inspection object W as shown in FIG. 11, for example. The outermost shape of the irradiation solid angle IS is determined by the aperture at the central portion of the first shielding mask M1. Furthermore, within this irradiation solid angle, solid angle regions IS1, IS2, and IS3 having different optical attributes are formed by the first filtering means F1, the solid angle regions IS1, IS2, and IS3 corresponding to the mask patterns F11, F12, and F13, respectively, of the first filtering means F1.

In contrast to the above-described lighting arrangement of the present invention that is capable of forming substantially uniform irradiation solid angles, in the case of a conventional lighting arrangement that uses only an ordinary light source surface, as shown in FIG. 5, irradiation solid angles IS of the inspection light have different shapes, sizes, and inclinations at different points on the inspection object W. This is because the irradiation solid angle IS at each point on the inspection object W is uniquely determined by the projection shape, size, and angle of the surface light source 1 when viewed from that point in the opposite direction to the lighting direction. On the other hand, the observation solid angle OS at each point on the inspection object is determined based on the relation between the pupil position, the pupil shape, and the pupil size of the imaging device C and that point on the inspection object. The brightness at each point that is detected by the imaging device C is determined by an inclusive relation between a solid angle RS of reflected light or a solid angle TS of transmitted light, which directly reflects the irradiation solid angle IS at that point, and the observation solid angle OS. In FIG. 5, this inclusive relation differs from location to location, and it can be seen that, if changes in solid angles RS of reflected light or solid angles TS of transmitted light are small, it is difficult to obtain the same amounts of change in light at respective points in the inspection area.

In general, the degree of inclination of an observation solid angle other than the principal optical axis is determined by the characteristics of an imaging optical system, and changes concentrically from the principal optical axis, due to the properties of ordinary lenses. For such an imaging optical system, if it is desired to obtain a uniform change in light, in particular, a uniform amount of change with respect to a change in the inclination of the solid angle of reflected or transmitted light at each point on the inspection object, the inclination of the irradiation solid angle of the inspection light on the inspection object can be varied concentrically relative to the principal optical axis, and in this manner, a constant relation between the irradiation solid angle and the observation solid angle can be maintained at each point.

FIG. 6 shows the inspection system 200 that uses a portion of the inspection lighting device 100 of the first embodiment according to the present invention and that is constituted by the imaging device C. In this inspection system 200, with respect to the observation solid angles OS that are formed by the imaging device C at respective points on the inspection object, the position of the first shielding mask M1 and the first filtering means F1, or the third filtering means F3, is set shifted from the focal distance position of the lens 2, thereby making the optical axis of the solid angle RS of reflected light or the solid angle TS of transmitted light that directly reflects the irradiation solid angle IS at each point on the inspection object W coincide with the optical axis of the observation solid angle OS at that point. In this manner, when the solid angle RS of reflected light or the solid angle TS of transmitted light at each point on the inspection object W changes, this change can be captured as a change in the inclusive relation with the observation solid angle OS, that is, a change in brightness at the same rate of change at each point. At this time, if the imaging optical system is a telecentric optical system in which all of the optical axes of the observation solid angles OS at respective points on the inspection object, which are formed by the imaging device C, extend in the same direction, setting the position of the first shielding mask M1 and the first filtering means F1, or the third filtering means F3, at the focal distance position of the lens 2 and thereby orienting all of the optical axes of irradiation solid angles IS to be formed in the same direction makes it possible for the optical axes of the irradiation solid angles IS to coincide with the optical axes of the observation solid angles OS at the respective points on the inspection object W.

Here, the inclusive relation between the irradiation solid angle and the observation solid angle as well as brightness information obtained by the imaging device will be described using FIG. 10.

In FIG. 10($a$), attention is paid to a point P on the inspection object W, and assuming that inspection light having an irradiation solid angle IS is irradiated onto the point P, how the brightness of the point P changes when a surface of the inspection object that contains the point P is partially inclined by $\varphi$ is shown. More specifically, how the relation between a solid angle and an observation solid angle OS that is formed at the point P by the imaging device C changes when a solid angle RS of reflected light from the point P changes to a solid angle RS' is shown.

In FIG. 10($a$), the shapes and sizes of the solid angles RS and RS' of reflected light from the point P are equal to those of the irradiation solid angle IS of the inspection light incident on the point P. Also, with regard to the inclination of the solid angle RS of the reflected light, the solid angle RS is inclined from a normal line to the point P by an angle equal to the inclination $\theta$ of the irradiation solid angle IS of the inspection light in a direction in which the solid angle RS and the irradiation solid angle IS of the inspection light are line symmetrical with respect to the normal line. At this time, if the optical axis of the observation solid angle OS that is formed at the point P by the imaging device C coincides with the optical axis of the solid angle RS of the reflected light, and the size of the observation solid angle OS is smaller than that of the solid angle RS of the reflected light, the brightness of the point P that is detected by the imaging device C is limited by the size of that observation solid angle OS and does not change even when the solid angle RS of the reflected light is inclined, as long as the above-described inclusive relation remains unchanged. However, it is assumed that the optical energies within the irradiation solid angle IS and the solid angles RS and RS' of the reflected light are uniformly distributed within the respective solid angles.

Next, in FIG. 10(a), a case where the surface of the inspection object W that contains the point P is partially inclined by φ is considered. In this case, the solid angle RS of reflected light from the point P will be inclined by 2φ like the solid angle RS' indicated by the dotted lines in the diagram. At this time, if the solid angle RS' of reflected light from the point P does not have an inclusive relation with the observation solid angle OS that is formed at the point P by the imaging device C, the brightness of the point P when seen from the imaging device C is 0. However, if the solid angle RS' has a partial inclusive relation with the observation solid angle OS that is formed at the point P by the imaging device C, light that is contained in a solid angle portion where the solid angle RS' and the observation solid angle OS overlap each other is reflected in the brightness of the point P. That is to say, if the half plane angle of the solid angle RS' of light reflected from the point P is larger than the angle obtained by subtracting the half plane angle of the observation solid angle OS from the inclination angle 2φ of the reflected light and smaller than the sum of the half plane angle of the observation solid angle OS and the inclination angle 2φ of the reflected light, the brightness of the point P changes in accordance with the inclination angle 2φ of the reflected light. However, if the half plane angle of the irradiation solid angle IS is larger than the sum of the half plane angle of the observation solid angle OS and the inclination angle 2φ of the reflected light that is generated by partially inclining the inspection object W, the brightness of the point P remains unchanged. Moreover, if the half plane angle of the observation solid angle OS is larger than the sum of the inclination angle 2φ of the reflected light and the half plane angle of the solid angle RS of the reflected light, the brightness of the point P also remains unchanged. This shows that the brightness of the point P is determined eventually by the inclusive relation between the solid angle RS of the reflected light from the point P and the observation solid angle OS at the point P and that a change in the brightness of the point P can be controlled by setting the relation between the irradiation solid angle IS of the inspection light irradiated onto the point P and the observation solid angle OS at the point P in terms of their shapes, sizes, and inclinations.

FIG. 10(b) is a cross-sectional view taken along a plane containing the irradiation optical axis of the inspection light, the normal line to the point P, and the optical axis of the reflected light from the point P in FIG. 10(a). The inclinations of the elements and the inclusive relation thereof can be more quantitatively seen from this diagram. It should be noted, however, that FIG. 10(b) illustrates a case in which the observation solid angle OS is larger than the irradiation solid angle IS, that is, the solid angle RS of the reflected light. If the inspection object W is inclined, and the solid angle RS of the reflected light from the point P thus changes to the solid angle RS' indicated by the dotted lines, the inclusive relation with the observation solid angle OS is no longer present in this diagram, and the optical energy within the observation solid angle OS becomes 0. Accordingly, even when light contained in this observation solid angle OS is converged again at the point for imaging, the point P is seen as being totally black. However, in this case as well, generating an inclusive relation between the solid angle RS of the reflected light and the observation solid angle OS by adjusting the relation between the irradiation solid angle IS and the observation solid angle OS allows the brightness of the point P to change in accordance with a change in the size of the overlapping portion between the solid angle RS and the observation solid angle OS.

In FIG. 10(b), when the observation solid angle OS has the same shape and size as the irradiation solid angle IS and the same inclination as the solid angle RS of the reflected light from the point P, if the inspection object W is inclined even slightly from this state, the overlapping portion between the observation solid angle OS and the solid angle RS of the reflected light decreases at least by an amount corresponding to the amount of this inclination, and the brightness of the point P as seen via the observation solid angle OS changes accordingly. Moreover, the smaller the solid angles, the larger the amount of change in the brightness of the point P with respect to a fixed angle of inclination of the inspection object W, and conversely, the larger the solid angles, the smaller the amount of change in the brightness of the point P with respect to a fixed angle of inclination of the inspection object W. Furthermore, precision detection of a feature point that could not be stably detected up until now is made possible by appropriately setting the shapes, sizes, inclinations, and the like of the irradiation solid angle IS and the observation solid angle OS in accordance with a change in light generated at a desired feature point on the inspection object. The present invention focused on this principle, and thus, an inspection lighting device capable of accurately controlling the shape, size, and inclination of an irradiation solid angle was conceived.

Next, with reference to FIG. 11, assuming that an irradiation solid angle of light irradiated onto an inspection object contains solid angle regions having different optical attributes, how the brightness of the point P on the inspection object changes in accordance with the inclusive relation between a solid angle of reflected light that is reflected from the point P and an observation solid angle that is formed at the point P by the imaging device C will be described.

The inside of an irradiation solid angle IS shown in FIG. 11 is formed of solid angle regions IS1, IS2, and IS3 having different optical attributes. At this time, a solid angle RS of reflected light that is reflected from the point P on the inspection object W is the same as the irradiation solid angle IS, the optical axis of the solid angle RS and the optical axis of the irradiation solid angle IS are line symmetrical with respect to a normal line to the point P on the inspection object W, and solid angle regions RS1, RS2, and RS3 are also formed within the solid angle RS of the reflected light, the solid angle regions RS1, RS2, and RS3 corresponding to and having the same optical attributes as the respective solid angle regions IS1, IS2, and IS3, which are formed within the irradiation solid angle and have different optical attributes.

In FIG. 11, for the sake of simplicity, a case in which the observation solid angle OS that is formed at the point P on the inspection object W by the imaging device C is sufficiently small relative to the solid angle RS of the reflected light and the solid angle regions RS1, RS2, and RS3, which are formed within the solid angle RS of the reflected light and have different optical attributes, is considered. FIG. 11(a) illustrates a case in which the observation solid angle OS is entirely included in the solid angle region RS1. At this time, if the imaging device C is provided with a second filtering means that can selectively detect light rays having different optical properties, the brightness of the point P on the inspection object is determined as being a certain degree of brightness based on only light rays having the optical attribute corresponding to the solid angle region RS1.

Next, as shown in FIG. 11(b), a case in which the surface of the inspection object W is inclined by φ is considered. In this case, the optical axis of the solid angle RS of the reflected light is inclined by 2φ, and the observation solid angle OS is included in the solid angle region RS3 having the distinct optical properties. That is to say, at this time, the brightness of the point P on the inspection object is determined as being a certain degree of brightness based on only light rays having the optical attribute corresponding to the solid angle region RS3.

Now, in order to facilitate understanding, it is assumed that the solid angle regions RS1, RS2, and RS3 having different optical properties shown in FIG. 11 correspond to, for example, blue light, green light, and red light, respectively, and the imaging device C serves as a color camera. Then, the point P on the inspection object W can be seen in blue with a certain degree of brightness in the case of FIG. 11(a), and can be seen in red with a certain degree of brightness in the case of FIG. 11(b). Moreover, when a case in which the inclination angle φ of the inspection object W gradually increases is considered, as the inclination angle increases, the point P on the inspection object W gradually turns from blue to green and then continuously changes from green to red. Although an irradiation solid angle in which no solid angle regions having different optical attributes are contained provides only contrast information that is determined by the inclusive relation between that irradiation solid angle and an observation solid angle, the present invention makes it possible to continuously capture a wider range of inclination angles φ of the inspection object W.

Next, the half mirror 4 of the present invention is a very thin circular component supported by a substantially square frame. With use of this half mirror 4, a separation portion between the front and back surfaces, where reflection or transmission occurs, of the half mirror 4 can be formed to be very thin, so that ghosts that may be caused by slight refraction, internal reflection, and the like during transmission of reflected light from the inspection object W through the half mirror 4 can be minimized.

The first shielding mask and the second shielding mask may each be an aperture stop with a plurality of blades, which is a commonly-employed optical material, or may be a combination of a very thin shielding plate having any desired aperture and an aperture stop. Furthermore, a member such as a liquid crystal member in which an aperture can be electronically set may also be used.

Moreover, in another embodiment that is different in terms of the aperture of the first shielding mask, for example, the aperture may be formed into an elliptical shape or an elongated slit-like shape, instead of a circular shape. With this configuration, in detection of a feature point on the inspection object, anisotropy can be imparted to the detection sensitivity. That is to say, at this time, the irradiation solid angle at each point on the inspection object is widened in the same longitudinal direction as the slit of the first shielding mask and is very narrow in the transverse direction. In this case, the detection sensitivity with respect to an inclination of the inspection object in the longitudinal direction is low, and only the detection sensitivity with respect to the transverse direction can be set high. However, in this case, it is necessary to set the shape, size, and inclination of the observation solid angle that is formed at each point on the inspection object by the imaging device in accordance with those of the irradiation solid angle with respect to the transverse direction so as to be substantially equal relative to those of the irradiation solid angle. Alternatively, if the size of the observation solid angle that is formed at each point on the inspection object by the imaging device is set to be sufficiently small, a threshold value for the inclination to be detected can be set because the irradiation solid angle is widened.

Moreover, in yet another embodiment that is different in terms of the aperture of the first shielding mask, for example, the aperture may include a shielding portion and an aperture that are concentric with each other. With this configuration, if appropriate widths thereof are set, with respect to a partial inclination of the inspection object, detection of only a certain inclination angle range can be performed. Also, if a required width is set in a required direction, anisotropy can be imparted to the detection angle. Alternatively, if multiple inspection lighting arrangements such as the above-described one are provided, classification and detection can be performed in accordance with the degree of inclination of the surface. In addition, if the above-described member such as a liquid crystal member in which an aperture can be electronically set is used as the first shielding mask, a plurality of types of contrast information can be obtained by dynamically switching the patterns of the aperture, making it possible to perform even more detailed classification and detection.

Furthermore, with respect to the first filtering means F1, the wavelength band, the polarization state, the luminance, and the like are conceivable as examples of the optical attributes. For example, when a light source emitting white light is used as the light source 1, the first filtering means F1 can form any solid angle regions constituted by light in different wavelength bands. Thus, light can be irradiated with different patterns and different wavelength bands from any direction in any shape at the same time, and furthermore, under exactly the same conditions at every point within the field-of-view range of the inspection object W. In addition, if a member, such as a color liquid crystal member, in which a pattern, the transmittance, or the like can be electronically set is used as the first filtering means F1, a plurality of types of contrast information can be obtained by dynamically switching patterns of the filter, so that even more detailed classification and detection can be performed.

Moreover, as a configuration example of the second filter, the second filter may be clearly divided into solid angle regions having different optical attributes, or may have gradations such that the optical attributes gradually change from one to another. With this configuration, if, for example, the luminance of reflected light or transmitted light from the inspection object differs depending on the irradiation angle or the observation angle, the luminance can be made uniform, or conversely, the luminance can be varied. For example, it is possible to freely adjust the difference in luminance between light that is directly reflected from the surface of the inspection object W and light from a portion, such as a scratch, that emits scattered light. This can be realized by reducing the light amount in an irradiation solid angle region corresponding to the angular range of light that is directly reflected from the surface of the inspection object W as regularly reflected light, and gradually increasing the light amounts in the other solid angle regions.

A significant effect of the present invention is that, since any desired pattern can be formed by the first shielding mask and the first filtering means, irradiation light can be irradiated with irradiation solid angles of any desired shapes and also with their optical attributes being varied in any desired manner, and therefore, can be irradiated under exactly the same conditions at all positions across the field-of-view range on the inspection object W to be imaged by the imaging device C, and, furthermore, the optical axes and the irradiation solid angles of the irradiated light can be set to be suitable for the optical characteristics of the imaging device. FIG. 12(a) illustrates irradiation solid angles IS and IS' that are formed at different positions P and P' on an inspection object W when the inspection object W is irradiated using commonly-employed conventional lighting. It can be seen that the two irradiation solid angles have different shapes and different optical axes. FIG. 12(b) illustrates a mode of irradiation light according to the present invention. The irradiation light can be irradiated under exactly the same conditions at all positions across the entire field-of-view range on the inspection object W. In this manner, a significant effect can be expected to be achieved in particular in a bright field lighting method, in which reflected light or transmitted light returned from the inspection object W is observed. Here, the reflected light refers to regularly reflected light returned from a mirror surface or the like, and the transmitted light refers to regularly transmitted light transmitted through a transparent object. Moreover, in a dark field lighting method as well, in which scattered light is observed, since the scattered light often varies depending on the optical attribute and the irradiation solid angle of irradiated light, the present invention enables detection of a slight change, which has since been unable to be realized by conventional lighting.

FIG. 13 illustrates examples of optional patterns that may be formed by the first shielding mask and the first filtering means, or the third filtering means, and respective resulting shapes of the irradiation solid angle. FIGS. 13(d) and 13(h) show patterns that are formed by the first shielding mask and the first filtering means and that contain solid angle regions having different optical attributes. However, in the other patterns as well, the first filtering means may cause all or part of the irradiation solid angle to have an optical attribute of a certain range, or the shielding portion M1 may transmit only light having a specific attribute, and in this case, the irradiation solid angle IS constitutes a boundary between solid angle regions having different optical properties.

Moreover, since the second shielding mask is imaged onto the inspection object, it is possible to set a distinct optical attribute for each irradiation area of the inspection light by providing, in the aperture of the shielding mask, a fourth filtering means that transmits only light having a specific attribute. At this time, if it is unnecessary to set an area that is not irradiated, an irradiation area may be set using only the fourth filtering means, for each specific optical attribute of light transmitted therethrough.

Furthermore, if the above-described member such as a liquid crystal member in which an aperture can be electronically set is used as the second shielding mask, the irradiation area of the inspection light can be changed by dynamically switching the patterns of the aperture, so that even when the inspection object requires different irradiation areas, inspection light can be irradiated in a manner suited to each of those areas, whereby a plurality of types of contrast information can be obtained.

Furthermore, if the surface light source is configured by combining a color liquid crystal or the like that is capable of dynamically changing the emission light wavelength distribution, the brightness distribution, and the polarization state distribution on the irradiating face with a white light source, an even wider variety of inspection objects can be supported.

Aside from the above, various modifications and combinations of embodiments can be made without departing from the gist of the present invention.

List of Reference Numerals

| 200 | Inspection system |
| --- | --- |
| 100 | Inspection lighting device |
| 1 | Surface light source |
| 11 | Light-emitting face |

-continued

List of Reference Numerals

| 2 | Lens |
| --- | --- |
| 4 | Half mirror |
| C | Imaging device |
| L1 | Irradiation light path |
| L2 | Reflection/transmission light path |
| M1 | First shielding mask (and its shielding portion) |
| F1 | First filtering means |
| F11 | Portion of first filtering means that transmits light having certain optical attribute 1 |
| F12 | Portion of first filtering means that transmits light having certain optical attribute 2 |
| F13 | Portion of first filtering means that transmits light having certain optical attribute 3 |
| F2 | Second filtering means |
| F3 | Third filtering means |
| F4 | Fourth filtering means |
| M2 | Second shielding mask |
| W | Inspection object |
| P | Certain point on inspection object W |
| P' | Another point on inspection object W |
| P1 | Object-side focus of lens 2 |
| P2 | Point having the same distance as P1 from lens 2 |
| P3 | Point having the same distance as P1 from lens 2 |
| P4 | Arbitrary point farther away than object-side focus from lens 2 |
| P5 | Arbitrary point farther away than object-side focus from lens 2 |
| IS | Irradiation solid angle |
| IS' | Another irradiation solid angle |
| IS1 | Solid angle region 1 having distinct optical attribute within irradiation solid angle |
| IS2 | Solid angle region 2 having distinct optical attribute within irradiation solid angle |
| IS3 | Solid angle region 3 having distinct optical attribute within irradiation solid angle |
| OS | Observation solid angle |
| RS | Solid angle of reflected light |
| RS' | Solid angle of reflected light |
| RS1 | Solid angle region 1 having distinct optical attribute within solid angle of reflected light |
| RS2 | Solid angle region 2 having distinct optical attribute within solid angle of reflected light |
| RS3 | Solid angle region 3 having distinct optical attribute within solid angle of reflected light |
| TS | Solid angle of transmitted light |

The invention claimed is:

1. An inspection lighting device configured to irradiate inspection light onto an inspection object, the inspection lighting device comprising:
    a surface light source for emitting inspection light;
    a lens disposed between the surface light source and the inspection object and configured to form on the inspection object an irradiation solid angle of light that is emitted from the surface light source and irradiated onto the inspection object as the inspection light; and
    a first filter disposed between the surface light source and the lens and in front of or behind a focus position of the lens, centered around the focus position,
    the first filter comprises a plurality of filter areas having different optical attributes, and simultaneously forms a plurality of solid angle regions having different optical attributes within the irradiation solid angle of the inspection light irradiated onto each point on the inspection object;
    wherein the light that passes through the first filter forms the same irradiation solid angle on each point of the inspection object, such that within each irradiation solid angle a plurality of irradiation solid angle regions are formed in the same solid angle range by the first filter, and
    wherein a shape, a size, or an inclination of the solid angle regions and an optical attribute such as a wavelength band, a polarization state, or a light amount can be set.

2. The inspection lighting device according to claim 1, further comprising:
- at least one of a shielding mask and a second filter at a position between the surface light source and the first filter and in the vicinity of a position at which the at least one of the shielding mask and the second filter is imaged onto the inspection object by the lens,
- wherein an irradiation area, an irradiation shape, an irradiation pattern, or an optical attribute of the inspection light irradiated onto the inspection object can be set as desired by using the second shielding mask or the second filter.

3. The inspection lighting device according to claim 2, further comprising:
- a half mirror disposed between the lens and the inspection object in the inspection lighting device and configured to change an irradiation direction of the inspection light and to transmit light from the inspection object so that the light can be imaged by the imaging device,
- wherein optical axes of the solid angle regions as the irradiation solid angle of the inspection light at each point on the inspection object substantially coincides with an optical axis of the observation solid angle of the imaging device at that point on the inspection object.

4. The inspection lighting device according to claim 3, wherein the inspection lighting device is configured to be applied to an inspection system constituted by the inspection lighting device and an imaging device for imaging light reflected, transmitted, or scattered by the inspection object, and
- with respect to an observation solid angle that is formed at each point on the inspection object when the imaging device images light from the inspection object, the shape, the size, or the inclination of the solid angle regions and the optical attribute contained in the solid angle regions can be set such that a desired change can be generated in a contrast at that point.

5. An inspection system comprising:
- the inspection lighting device according to claim 4; and
- an imaging device for imaging light reflected, transmitted, or scattered by the inspection object,
- wherein, in an irradiation solid angle of inspection light irradiated onto the inspection object by the inspection lighting device, a shape, a size, or an inclination of the solid angle regions at each point on the inspection object is set to be suitable for acquiring desired gradation information based on a shape, a size, or an inclination of an observation solid angle of the imaging device at that point on the inspection object, or the shapes, the sizes, or the inclinations of the solid angle regions and the observation solid angle are set to be substantially uniform relative to each other.

6. An inspection system comprising:
- the inspection lighting device according to claim 3; and
- an imaging device for imaging light reflected, transmitted, or scattered by the inspection object,
- wherein, in an irradiation solid angle of inspection light irradiated onto the inspection object by the inspection lighting device, a shape, a size, or an inclination of the solid angle regions at each point on the inspection object is set to be suitable for acquiring desired gradation information based on a shape, a size, or an inclination of an observation solid angle of the imaging device at that point on the inspection object, or the shapes, the sizes, or the inclinations of the solid angle regions and the observation solid angle are set to be substantially uniform relative to each other.

7. The inspection lighting device according to claim 2,
- wherein the inspection lighting device is configured to be applied to an inspection system constituted by the inspection lighting device and an imaging device for imaging light reflected, transmitted, or scattered by the inspection object, and
- with respect to an observation solid angle that is formed at each point on the inspection object when the imaging device images light from the inspection object, the shape, the size, or the inclination of the solid angle regions and the optical attribute contained in the solid angle regions can be set such that a desired change can be generated in a contrast at that point.

8. An inspection system comprising:
- the inspection lighting device according to claim 7; and
- an imaging device for imaging light reflected, transmitted, or scattered by the inspection object,
- wherein, in an irradiation solid angle of inspection light irradiated onto the inspection object by the inspection lighting device, a shape, a size, or an inclination of the solid angle regions at each point on the inspection object is set to be suitable for acquiring desired gradation information based on a shape, a size, or an inclination of an observation solid angle of the imaging device at that point on the inspection object, or the shapes, the sizes, or the inclinations of the solid angle regions and the observation solid angle are set to be substantially uniform relative to each other.

9. An inspection system comprising:
- the inspection lighting device according to claim 2; and
- an imaging device for imaging light reflected, transmitted, or scattered by the inspection object,
- wherein, in an irradiation solid angle of inspection light irradiated onto the inspection object by the inspection lighting device, a shape, a size, or an inclination of the solid angle regions at each point on the inspection object is set to be suitable for acquiring desired gradation information based on a shape, a size, or an inclination of an observation solid angle of the imaging device at that point on the inspection object, or the shapes, the sizes, or the inclinations of the solid angle regions and the observation solid angle are set to be substantially uniform relative to each other.

10. The inspection lighting device according to claim 1, further comprising:
- a half mirror disposed between the lens and the inspection object in the inspection lighting device and configured to change an irradiation direction of the inspection light and to transmit light from the inspection object so that the light can be imaged by the imaging device,
- wherein optical axes of the solid angle regions as the irradiation solid angle of the inspection light at each point on the inspection object substantially coincides with an optical axis of the observation solid angle of the imaging device at that point on the inspection object.

11. The inspection lighting device according to claim 10,
- wherein the inspection lighting device is configured to be applied to an inspection system constituted by the inspection lighting device and an imaging device for imaging light reflected, transmitted, or scattered by the inspection object, and
- with respect to an observation solid angle that is formed at each point on the inspection object when the imaging device images light from the inspection object, the shape, the size, or the inclination of the solid angle regions and the optical attribute contained in the solid angle regions can be set such that a desired change can be generated in a contrast at that point.

12. An inspection system comprising:
the inspection lighting device according to claim 11; and
an imaging device for imaging light reflected, transmitted, or scattered by the inspection object,
wherein, in an irradiation solid angle of inspection light irradiated onto the inspection object by the inspection lighting device, a shape, a size, or an inclination of the solid angle regions at each point on the inspection object is set to be suitable for acquiring desired gradation information based on a shape, a size, or an inclination of an observation solid angle of the imaging device at that point on the inspection object, or the shapes, the sizes, or the inclinations of the solid angle regions and the observation solid angle are set to be substantially uniform relative to each other.

13. An inspection system comprising:
the inspection lighting device according to claim 10; and
an imaging device for imaging light reflected, transmitted, or scattered by, the inspection object,
wherein, in an irradiation solid angle of inspection light irradiated onto the inspection object by the inspection lighting device, a shape, a size, or an inclination of the solid angle regions at each point on the inspection object is set to be suitable for acquiring desired gradation information based on a shape, a size, or an inclination of an observation solid angle of the imaging device at that point on the inspection object, or the shapes, the sizes, or the inclinations of the solid angle regions and the observation solid angle are set to be substantially uniform relative to each other.

14. The inspection lighting device according to claim 1, wherein the inspection lighting device is configured to be applied to an inspection system constituted by the inspection lighting device and an imaging device for imaging light reflected, transmitted, or scattered by the inspection object, and
with respect to an observation solid angle that is formed at each point on the inspection object when the imaging device images light from the inspection object, the shape, the size, or the inclination of the solid angle regions and the optical attribute contained in the solid angle regions can be set such that a desired change can be generated in a contrast at that point.

15. An inspection system comprising:
the inspection lighting device according to claim 14; and
an imaging device for imaging light reflected, transmitted, or scattered by the inspection object,
wherein, in an irradiation solid angle of inspection light irradiated onto the inspection object by the inspection lighting device, a shape, a size, or an inclination of the solid angle regions at each point on the inspection object is set to be suitable for acquiring desired gradation information based on a shape, a size, or an inclination of an observation solid angle of the imaging device at that point on the inspection object, or the shapes, the sizes, or the inclinations of the solid angle regions and the observation solid angle are set to be substantially uniform relative to each other.

16. An inspection system comprising:
the inspection lighting device according to claim 1; and
an imaging device for imaging light reflected, transmitted, or scattered by the inspection object,
wherein, in an irradiation solid angle of inspection light irradiated onto the inspection object by the inspection lighting device,
a shape, a size, or an inclination of the solid angle regions at each point on the inspection object is set to be suitable for acquiring desired gradation information based on a shape, a size, or an inclination of an observation solid angle of the imaging device at that point on the inspection object, or the shapes, the sizes, or the inclinations of the solid angle regions and the observation solid angle are set to be substantially uniform relative to each other.

17. An inspection lighting device configured to irradiate inspection light onto an inspection object, the inspection lighting device comprising:
a surface light source for emitting inspection light;
a lens disposed between the surface light source and the inspection object and configured to form on the inspection object an irradiation solid angle of light that is emitted from the surface light source and irradiated onto the inspection object as the inspection light; and
a first filter held between the surface light source and the lens by a position change unit movable along an optical axis of the inspection light to a position in front of or behind a focus position of the lens, centered around the focus position,
the first filter comprises a plurality of filter areas having different optical attributes, and the first filter simultaneously forms a plurality of solid angle regions having different optical attributes within the irradiation solid angle of the inspection light irradiated onto each point on the inspection object; and adjusts an axial direction of the solid angle of irradiation formed at each point on the inspection object,
wherein a shape, a size, or an inclination of the solid angle regions and an optical attribute such as a wavelength band, a polarization state, or a light amount can be set.

18. An inspection system comprising:
a surface light source for emitting inspection light onto an inspection object;
a lens disposed between the surface light source and the inspection object and configured to form on the inspection object an irradiation solid angle of light that is emitted from the surface light source and irradiated onto the inspection object as the inspection light;
an imaging device for imaging light reflected or transmitted by the inspection object, and
a first filter held between the surface light source and the lens by a position change unit movable along an optical axis of the inspection light to a position in front of or behind a focus position of the lens, centered around the focus position,
the first filter comprises a plurality of filter areas having different optical attributes, and simultaneously forms a plurality of solid angle regions having different optical attributes within the irradiation solid angle of the inspection light irradiated onto each point on the inspection object, and
an axial direction of the irradiation solid angle formed at each point on the inspection object and an axial direction of the observation solid angle of the imaging device with respect to the inspection object are made to coincide with each other.

* * * * *